(12) United States Patent
Herrmann

(10) Patent No.: US 6,949,680 B2
(45) Date of Patent: Sep. 27, 2005

(54) KETONES AS PRECURSORS OF ACTIVE COMPOUNDS

(75) Inventor: Andreas Herrmann, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/270,224

(22) Filed: Oct. 15, 2002

(65) Prior Publication Data

US 2003/0129212 A1 Jul. 10, 2003

Related U.S. Application Data

(63) Continuation of application No. PCT/IB01/01021, filed on Jun. 11, 2001.

(30) Foreign Application Priority Data

Jun. 15, 2000 (WO) .................................. PCT/IB00/00804

(51) Int. Cl.$^7$ ........................ C07C 45/00; C07D 211/72; A61K 7/46; A01N 25/34

(52) U.S. Cl. ........................ 568/327; 568/329; 568/331; 568/336; 568/337; 546/301; 512/8; 512/16; 512/21; 510/301; 424/403; 424/404

(58) Field of Search .............................. 568/327, 329, 568/331, 335, 337; 546/301; 512/8, 14, 21; 510/301; 424/403, 404

(56) References Cited

U.S. PATENT DOCUMENTS 3,961,040 A    6/1976  Rabussier et al. ............ 424/33
6,258,854 B1 *  7/2001  Anderson et al.

FOREIGN PATENT DOCUMENTS

| EP | 0 045 534 | 2/1982 |
| EP | 0 983 990 A2 | 3/2000 |
| WO | WO 98/07405 | 2/1998 |
| WO | WO 99/609990 | 3/2000 |

OTHER PUBLICATIONS

Maezaki et al. Studies on Intramolecular Alkylation of an alpha–Sulfinyl Vinylic Cabanion: a Novel Route to Chiral 1–Cycloalkenyl Sulfoxides. Tetrahedron, 56 (40), 2000, p 7927–7945.*
Hong et al. Hydroiminoacylation of Allyl and Homoallyl Alcohol Derivatives with Benzaldimine and Solvolysis or Hydroacylated Products. Bulletin of the Korean Chemical Society (1995), 16 (4), p 363–369.*
Axiotis et al. Action of aromatic organometallic reagents on RO–(CH2)n–CN oxygenated nitriles. Journal of Organometallic Chemistry (1979), vol. 166 (1). p 87–100.*
Taylor et al. Polystyrene–bound phenylseleninic acid: catalytic oxidations of olefins, ketones, and aromaatic systems. Journal of Organic Chemistry (1983), vol. 48 (26), p 5160–4.*
Mandolini et al. Ring closure reactions. Synthesis and ultraviolet spectra of macrocyclic aromatic ethers. Journal of Organic Chemistry (1977), vol. 42 (17) p 2840–3.*
P.J. Wagner, XP–002193367, "Intramolecular Triplet Energy Transfer in Flexible Molecules: Electronic, Dynamic, and Structural Aspects", J. Am. Chem. Soc., vol. 41, No. 121, pp. 9626–9635 (1999).

(Continued)

Primary Examiner—James O. Wilson
Assistant Examiner—Sikarl A. Witherspoon
(74) Attorney, Agent, or Firm—Winston & Strawn LLP

(57) ABSTRACT

A compound of formula

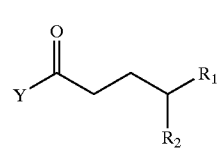

(I)

wherein Y represents a pyridyl group, or a phenyl group of formula

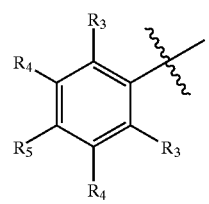

(Ia)

wherein $R_3$ represents a hydrogen atom, a $CF_3$ group or an alkoxy group, $R_4$ represents a hydrogen atom, an alkyl group, or a $CF_3$ group, $R_5$ represents a hydrogen atom, an alkyl group, a $CF_3$ group or an alkoxy group, and $R_1$ and $R_2$ are the substituents of a terminal alkene of formula

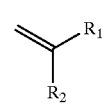

(i)

wherein $R_1$ represents an alkyl or alkylene group, a mono- or poly-cycloalkyl group, or a phenyl group that optionally includes one or several hetero-atoms of oxygen, nitrogen, phosphorous or sulfur; $R_2$ represents a hydrogen atom, an alkyl or alkylene group, a mono- or poly-cycloalkyl group, or a phenyl group that optionally includes one or several hetero-atoms of oxygen, nitrogen, phosphorous and sulfur. This compound is capable of releasing, upon an exposure to light, an active compound such as a perfume and can be advantageously used in the treatment of any surface in order to perfume it through the controlled release of a perfumed molecule.

14 Claims, 2 Drawing Sheets

OTHER PUBLICATIONS

M. Nakamura et al., XP–002193368, "Effects of methylene chains on photoreactions of diphenylaLkanediones and phenylalkenones", J. Am. Chem. Soc., Perkin Trans. 1, , pp. 415–420 (2000).

Ivan et al., Abstract—XP–002193369, "n Participation and secondary deuterium isotope effects in solvolysis of 1–aryl–4–methoxy–1–butyl chlorides", J. Am. Chem. Soc., vol. 44, No. 23, pp. 4091–4096–9635 (1979).

H. Jun–Bae et al., Abstract—XP–002193370, "Hydroiminoacylation of allyl and homoallyl alcohol derivatives with benzaldimine and solvolysis of hydroacylated products", Bull Korean Chem. Soc., vol. 16, No. 4, pp. 4091–363–369 (1995).

Luiz Dias et al., Abstract–XP–002193371, "Conjugate reduction of alpha., beta.–unsaturated carbonyl compounds, selective inhibition of benzyl either hydrogenolysis by NH4OH/MeOH", J. Braz. Chem. Soc., vol. 9, No. 1, pp. 97–99 (1998).

Fuerstner et al., XP–000872949, "Titanium–induced syntheses of Furans, Benzofurans and Idoles", Tetrahedron Elsevier Science Publishers, vol. 48, No. 29, pp. 5591–6010 (1992).

Murray et al, Abstract x{P002160202, "Alarm pheromones utilization in evaluation of olfactory theories", J. Insect Physiol, vol. 17, No. 12, pp. 5900–5902 (1971).

Epstein et al., "The synthesis of a Photolabile Detergent and its use in the isolation and characterization of Protein", Analytical Biochemistry, Vo. 199, pp. 304–312 (1982).

P. Wagner et al., "Type II photoelimination and Photocyclization of Ketones" Acc. Chem. Res., vol. 4, pp. 168–177 (1979).

P. Wagner, "Chemistry of Excited Triplet Organic Carbonyl Compounds", Topics in Current Chem., vol. 66, pp. 1–51, (1976).

* cited by examiner

KETONES AS PRECURSORS OF ACTIVE COMPOUNDS

CROSS-REFERENCE TO RELATED APPLICATIONS

This application is a continuation of the US national stage designation of International application PCT/IB01/01021 filed Jun. 11, 2001, the entire content of which is expressly incorporated herein by reference thereto.

TECHNICAL FIELD

The present invention relates to compositions or products comprising phenyl and pyridyl ketones which can act as precursors of active compounds such as perfumes, masking agents, antimicrobial agents or insect repelling or attracting agents. In fact, these ketones are capable, upon exposure to light, of releasing in a controlled manner molecules presenting a specific activity, notably fragrant terminal alkenes. Thus, the system of the present invention allows to provide a specific effect, such as perfuming, coming from any kind of surface, by treating the latter with a precursor according to the invention and then exposing said surface to light.

BACKGROUND ART

Several systems for releasing fragrant compounds have been described in the prior art. Firmenich PCT publication WO 99/60990 describes a fragrance delivery system that releases fragrant alcohols, aldehydes or ketones upon exposure to light. The system of that publication comprises 2-benzoyl benzoates or α-keto esters which are used as fragrance precursors.

There exists, in perfumery, a particular interest in compounds which are capable of "fixing" fragrant molecules, for example by chemical bonding or intramolecular forces like adsorption, and releasing these fragrant molecules over a prolonged period of time, for example by the action of heat, enzymes, or even sunlight (fragrant molecules have to be volatile in order to be perceived). Although many known fragrant compounds show a good substantivity, i.e., they will remain on a surface to which they have been applied for several days and can hence be perceived over such a period of time, a great number of fragrant compounds are very volatile, and their characteristic odor can no longer be perceived several hours after their application.

It is thus desirable to dispose of fragrance delivery systems which are capable of releasing the fragrant compound or compounds in a controlled manner, maintaining a desired scent over a prolonged period of time.

Therefore, in view of their importance in the field of perfumery, systems allowing the slow release of fragrant compounds constitute an object of intensive research in order to find new precursors capable of releasing different odorous compounds.

Phenyl ketones are known to be photolabile molecules. In fact, the photochemistry of these compounds was extensively studied in the prior art. One can cite for instance P. J. Wagner, in Acc. Chem. Res., 1971, 4, 168–171, or in Top. Curr. Chem. 1976, 66, 1–52.

Moreover, W. W. Epstein et al. disclose in Anal. Biochem. 1982, 119, 304–312 the use of alkyl phenyl ketones as photolabile linkage inserted in a detergent in order to cleave the latter under photolysis and to form a water-soluble compound and an olefin.

However, the prior art does not disclose the use of phenyl ketones as precursors of fragrant compounds, masking agents, antimicrobial agents or other active compounds or as being part of perfuming, masking, antimicrobial, insect repelling or insect attracting compositions or products, the latter providing systems that are capable of slowly releasing the active compounds. This is the discovery of the present inventors.

SUMMARY OF THE INVENTION

Now, we have been able to establish that certain phenyl and pyridyl ketones can be advantageously used within the scope of the slow release of active compounds such as fragrant molecules, masking agents, antimicrobial agents or insect repelling or attracting agents. In fact, they constitute useful precursors of terminal alkenes.

The invention thus relates to a perfuming, masking, antimicrobial, insect repelling or attracting composition or article comprising, together with one or more perfuming ingredients, masking agents, antimicrobial agents, insect repelling or attracting ingredients, solvents or adjuvants of current use, at least one compound of formula

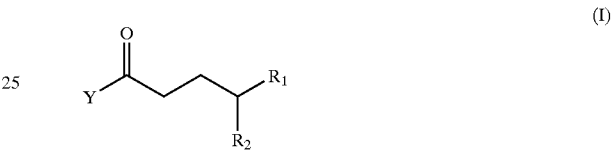

wherein Y represents a pyridyl group, or a phenyl group of formula

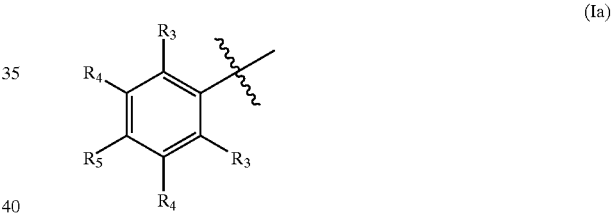

wherein $R_3$ represents a hydrogen atom, a $CF_3$ group or a linear or branched alkoxy group from $C_1$ to $C_{12}$, $R_4$ represents a hydrogen atom, a linear or branched alkyl group from $C_1$ to $C_4$, or a $CF_3$ group, $R_5$ represents a hydrogen atom, a linear or branched alkyl group from $C_1$ to $C_4$, a $CF_3$ group or a linear or branched alkoxy group from $C_1$ to $C_{12}$; and $R_1$ and $R_2$ are the substituents of a terminal alkene of formula

wherein $R_1$ represents a linear or branched alkyl or alkylene group from $C_1$ to $C_{35}$, an unsubstituted or substituted mono- or poly-cycloalkyl group having 3 to 8 carbon atoms, or an unsubstituted or substituted phenyl group, said alkyl, alkylene, mono- or poly-cycloalkyl and phenyl groups possibly comprising one or several hetero-atoms selected from the group consisting of oxygen, nitrogen, phosphorous and sulfur; and $R_2$ represents a hydrogen atom, a linear or branched alkyl or alkylene group from $C_1$ to $C_{35}$, an unsubstituted or substituted mono- or poly-cycloalkyl group from $C_3$ to $C_8$, or an unsubstituted or substituted phenyl group, said alkyl, alkylene, mono- or poly-cycloalkyl and phenyl groups possibly comprising one or several hetero-atoms selected from the group consisting of oxygen, nitrogen, phosphorous and sulfur.

The compounds of formula (I) are capable of releasing, under irradiation, an active alkene of formula (i). Non-limiting examples of active compounds released by the precursors of formula (I) include fragrant molecules, masking agents, antimicrobial agents or insect repelling or attracting compounds. Therefore, the nature of the substituents $R_1$ and $R_2$ is defined by the structure of the active molecule, namely the alkene of formula $CH_2=CR_1R_2$.

In a preferred embodiment of the invention, the active compound of formula (i) is a fragrant molecule. In this preferred embodiment, when $R_1$ and/or $R_2$ represent a linear or branched alkyl or alkylene group, the latter comprises from 1 to 20 carbon atoms.

DETAILED DESCRIPTION OF THE PREFERRED EMBODIMENTS

Figure 1:
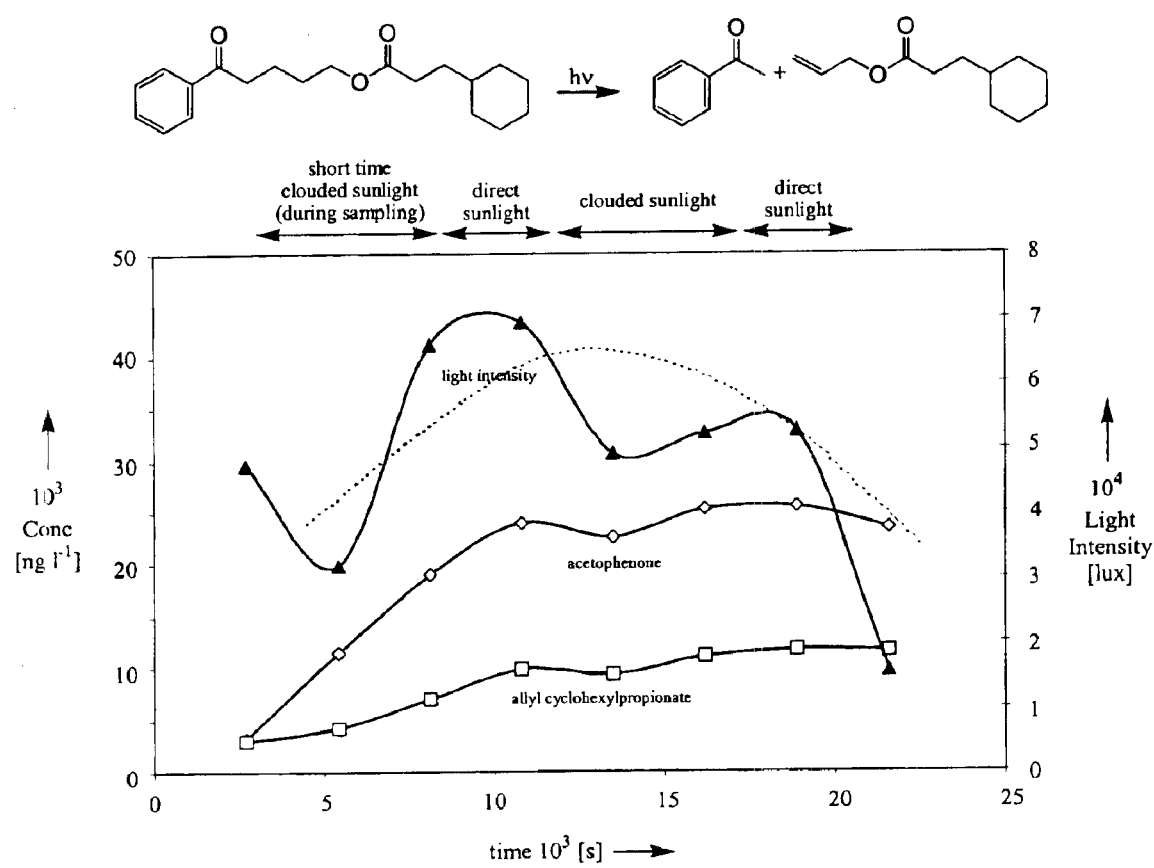
FIG. 1 is a graph that illustrates the formation of allyl cyclohexylpropionate and acetophenone from its precursor as measured in an all purpose cleaner by quantitative dynamic headspace analyses.

In a particular embodiment, the precursor of the perfuming, masking, antimicrobial, insect repelling or attracting alkene is of formula

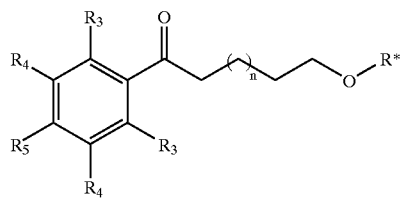

(II)

wherein $R_3$, $R_4$ and $R_5$ have the same meaning as in formula (I), n is an integer varying from 0 to 10, and R* represents a hydrogen atom, a linear or branched alkyl or alkylene group from $C_1$ to $C_{20}$, an unsubstituted or substituted mono- or poly-cycloalkyl group from $C_3$ to $C_8$, or an unsubstituted or substituted phenyl group, said alkyl, alkylene, mono- or poly-cycloalkyl and phenyl groups possibly comprising one or more hetero-atoms selected from the group consisting of oxygen, nitrogen, phosphorous and sulfur. The skilled artisan of course knows that when an alkylene group is present at least 2 carbon atoms are required.

In the above definitions, when reference is made to a masking agent, there is meant a compound that is able to enhance or to mask the characteristic odor of a material. Moreover, an antimicrobial agent is a compound that presents an antimicrobial activity, i.e. which is capable of reducing or preventing the development of microbial or bacterial activity. Examples of these compounds are given by J. J. Kabara in Cosmet. Sci. Technol. Ser. (16), 1997, 181–208, for example.

Similarly, when reference is made to a fragrant terminal alkene, there is meant an alkene which not only has an odor, but which is also known to a person skilled in the art as being useful as perfuming ingredient for the formulation of perfumes or perfumed articles. The criteria a useful perfuming ingredient has to fulfill are known to a person skilled in the art and include, amongst other, a certain originality of the odoriferous note, stability and a certain price/performance ratio. Non-limiting examples of alkenes that can be used within the scope of the invention will be mentioned below.

One of the advantages of the composition or product of the present invention lies in its capacity to slowly release the active alkene of formula (i) from which the phenyl or pyridyl ketone formula (I) is derived. The release occurs when said ketone is exposed to daylight in particular. Therefore, once applied in any kind of surface and upon absorption of energy from said light, the ketone undergoes a photoreaction in the course of which the active compound is released from the precursor molecule into the surroundings, thus generating a specific activity coming from the surface treated with the ketone of the invention. Said release occurs in a controlled manner, i.e., a more or less constant amount of active molecule is released over a period of time, without an initial burst of very intense action (odor, antimicrobial activity, repelling or attracting activity) which becomes rapidly imperceptible, as is the case with volatile terminal alkenes for instance. Because the release of the alkene can occur over several days or weeks, the use of the system of the present invention obviates the drawbacks of many molecules that show an important specific activity but are also very volatile.

Good examples of volatile fragrant molecules are styrene and allyl heptanoate which can only be perceived over a short period of, say, a few hours, when applied to the surface of, for example, tiles and windows in the course of a cleaning procedure using liquid cleaners; even in solution, the typical scent of said fragrant molecules disappears within several hours. It goes without saying that the concentration of the precursor in the application plays an important role in the time during which the active molecules can be perceived.

In an embodiment of the invention, the precursors of formula (I) are capable of releasing, under the action of light, a fragrant molecule of formula (i) wherein $R_1$ represents a linear or branched alkyl or alkylene group from $C_1$ to $C_{20}$, an unsubstituted or substituted mono- or poly-cycloalkyl group from $C_3$ to $C_8$, or an unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulphur; and $R_2$ represents a hydrogen atom, a linear or branched alkyl or alkylene group from $C_1$ to $C_{20}$, an unsubstituted or substituted mono- or poly-cycloalkyl group from $C_3$ to $C_8$, or an unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulfur. Perfuming compositions or perfumed products to which these precursors are added can thus release in a controlled and prolonged manner fragrant compounds upon exposure to light.

In a particularly advantageous embodiment, the composition or product of the invention in the form of a perfuming composition or product comprises at least one compound of formula (II) as defined above, the latter being susceptible of releasing, under the action of light, a compound of formula

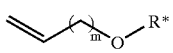
(ii)

wherein m varies from 1 to 10 and R* has the same meaning as in formula (II).

The compounds of formula (I) are capable of releasing a fragrant terminal alkene of formula (i) upon exposure to light. This system is particularly advantageous because the fragrant molecules, namely terminal alkenes, represent a class of volatile compounds of great importance in the field of perfumery. With the system of the present invention, the typical odor of terminal alkenes of formula (i) is perceived over a considerably longer period of time, when compared with the phenyl ketones or pyridyl ketones as such of the fragrance delivery system, which are not or are sparingly volatile. The fragrance delivery system remains as such on the surface to which it is applied or in the solution into which it is incorporated, and it is only upon exposure to light that the fragrant alkene is released. It is clear that this reaction can provide perceptible amounts of the alkene over days or weeks, depending, among other things, on the amount or the concentration of the fragrance precursor, the time of exposure to light, the intensity and wavelength of the latter. Moreover, and contrary to what has been disclosed in the prior art, the light induces, in this particular embodiment of the invention, a C—C cleavage. In other words, as the cleaved bond is not particularly labile, the precursor is thus very stable and can therefore be advantageously used in any kind of medium, particularly in an aggressive medium such as bleaches and bleaching detergents or antiperspirants, with a limited risk of reacting.

As non limiting examples of terminal alkenes which can be used in the present invention, one can cite allyl acetate, allyl anthranilate, allyl benzoate, allyl butanoate, allyl cyclohexaneacetate, allyl 3-cyclohexylpropanoate, allyl 2-furoate, allyl heptanoate, allyl hexanoate, allyl 2,4-hexadienoate, allyl 3-methylbutanoate, allyl nonanoate, 1-allyloxy-2-methoxybenzene, allyl phenoxyacetate, allyl phenylacetate, allyl phenyl-2-propenoate, allyl propanoate, allyl salicylate, 9-decen-1-ol, 9-decen-1-yl acetate, 9-decenylpropanoate, decyl vinyl ether, DYNASCONE® (1-(3,3-dimethyl-1-cyclohexen-1-yl)-4-penten-1-one; origin: Firmenich SA, Geneva, Switzerland), 1-(5,5-dimethyl-1-cyclohexen-1-yl)-4-penten-1-one, 3,7-dimethyl-1,6-octadien-3-ol, 1,5-dimethyl-1-vinyl-4-hexenyl acetate, 1,5-dimethyl-1-vinyl-4-hexenyl benzoate, 1,5-dimethyl-1-vinyl-4-hexenyl formate, 1,5-dimethyl-1-vinyl-4-hexenyl isobutyrate, 1,5-dimethyl-1-vinyl-4-hexenyl propanoate, 3,7-dimethyl-1-vinyloxy-2,6-octadiene, 3,7-dimethyl-1-vinyloxy-6-octene, 2-ethylhexyl 2-propenoate, ethyl 2-propenoate, ethyl 10-undecanoate, 6-hepten-2-ol, 8-nonen-1-ol, 1-octene, 1-penten-3-ol, 2-phenylethyl vinyl ether, 10-undecen-1-ol, vinyl acetate, vinylbenzene, 4-allyl-1,2-dimethoxybenzene, 1-allyl-4-methoxybenzene, 4-allyl-2-methoxyphenol, 1,3-dimethyl-3-butenylisobutyrate, 2,6-dimethyl-7-octen-2-ol, 1,8-p-menthadien-7-ol, 8-p-menthadien-2-one, 8-p-menthen-1-ol, 10-undecenal.

It is quite obvious, however, that the phenyl and pyridyl ketones comprised in the compositions of the invention can be derived from many other alkenes which the skilled person is quite able to choose from the general knowledge in the art and as a function of the olfactory, masking, antibacterial or insect repelling or attracting effect it is desired to achieve. The above list is more illustrative for fragrant compounds which are known to a person skilled in the art, and whose delivery can be improved, but it is clearly quite impossible to cite in an exhaustive manner all compounds of formula (i) which have a pleasant odor or an effective activity of some other useful type and the phenyl and pyridyl ketones which can be used in the compositions of the present invention.

The composition of the invention may comprise more than one alkene precursor of formula (I). For instance, a mixture of compounds of formula (I), being capable of releasing different fragrant alkenes, each possessing its proper odor, may be incorporated in a composition according to the invention so that, under the action of light, more than only one fragrant molecule is released, thus providing a fragrant harmony.

Moreover, when Y represents a phenyl group of formula (Ia), besides the desired alkenes, the photo-fragmentation of the precursor of formula (I) yields equimolar amounts of a substituted or unsubstituted acetophenone of formula

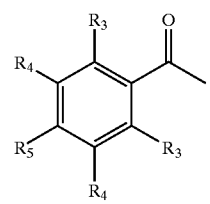
(Ib)

wherein the symbols have the same meaning as in formula (I), and which may also be useful as perfuming ingredients. Non-limiting examples of fragrant acetophenones include 1-(4-methoxyphenyl)-1-ethanone, 1-(4-methylphenyl)-1-ethanone, 1-phenyl-1-ethanone or 1-(4-tert-butylphenyl)-1-ethanone.

The compositions or products of the invention, comprising at least one compound of formula (I), or even a compound of formula (I) on its own, can be deposited on a surface which will be exposed to light, in order to perfume or attenuate undesirable odors or impart an antibacterial or insect repelling or attracting activity coming from the latter.

The present invention also relates to a method for generating a specific activity coming from a surface that comprises treating the latter with a compound of formula (I) and exposing said surface to light. Non-limiting examples of surfaces that may be treated with a compound of formula (I) include skin or hair, floors, windows, tiles, furniture, fabric or cloth, and plants such as flowers or trees.

The release of the above-mentioned active compounds from the precursors occurs upon the exposure to light, e.g., the normal daylight which can penetrate through ordinary windows in houses and which is not particularly rich in UV-radiation. It goes without saying that upon exposure to bright sunlight, in particular outdoors, the release of the active terminal alkene will occur faster and to a greater extent than upon exposure to the light indoors. Of course, the reaction that releases the active compound from the precursor can also be initiated by an appropriate artificial lamp.

The precursors of the present invention can be used in any application in which a prolonged, defined release of the above-mentioned fragrant, odor masking, antimicrobial or insect repelling or attracting compounds is desired. They mostly find use in functional perfumery, in products or articles that are exposed to daylight when in use or which are applied to other articles that thereafter are exposed to daylight. Suitable examples include air-fresheners in liquid and solid form which, with the precursors of the present invention, can still release a fragrance when conventional air-fresheners, i.e. those not containing a precursor of the present invention, are exhausted. Other kinds of aerosols, namely products such as antibacterial products or insect repelling or attracting products can also comprise a compound of formula (I). Other examples of products are various cleaners for the cleaning of surfaces of all kinds, e.g., window and household cleaners, all-purpose-cleaners and furniture polishes. The surfaces which have been cleaned with such cleaners will generate the specific activity of the released compound, such as the fragrance of a perfume, much longer than when cleaned with conventional cleaners. Other representative examples include detergents for fabric wash, fabric conditioners and fabric softeners which can also contain the precursors of the present invention and which products can be in the form of powders, liquids or tablets. The fabrics and clothes washed or treated with such detergents or softeners will diffuse the active compound even after having been stored for weeks or even months, in a dark place, like a wardrobe.

Examples of detergents which can be used include those described in WO 97/34986. Moreover, as softening bases one may select those described in the patents U.S. Pat. No. 4,137,180, U.S. Pat No. 5,236,615 or EP 799 885. Other typical compositions of detergents and softeners which may be used are described in works such as Ullmann's Encyclopedia of Industrial Chemistry, Vol. A8, pp. 315–448 (1985) and Vol. A25, pp. 747–817 (1994); E. W. Flick, Advanced Cleaning Product Formulations; Noyes Publication Park Ridge, N.J. (1989); M. S. Showell (Ed.) in Surfactant Science Series, Vol. 71; Powdered Detergents, Marcel Dekker, New York, N.Y. (1998); Proceeding of the $4^{th}$ World Conference on Detergents; Strategies for the $21^{st}$ century, A. Cahn (Ed.), AOCS Press, Champaign (1998). Of course, the use of the compounds of the invention is not limited to the products mentioned above.

The release of the active compound occurs in all the above-mentioned application examples. All possible types of window cleaners, household, all-purpose cleaners, air-fresheners, aerosols for a specific purpose, detergents, fabric washers and fabric softeners can be used with the precursors of the present invention, which have revealed themselves to be useful in all types of these above-mentioned application examples. The nature of the latter is quite immaterial as the person skilled in the art is able to adjust their composition or form, should this prove necessary, as a function of the effect desired and in much the same way as it does now with any current perfuming, masking, antimicrobial, insect repelling or attracting composition.

In the field of body care, the compositions comprising a fragrance precursor according to the present invention have shown themselves to be particularly appropriate for an application in the hair care area, and specific examples include shampoos, hair conditioners, in particular leave-on conditioners, hairsprays and other hair care products.

It can be said that generally all products which can be applied to a surface which is exposable to light can advantageously contain the precursors of the present invention. Examples include surfaces which belong to the human body, such as skin or hair, surfaces in buildings and apartments, like floors, windows, tiles or furniture, or surfaces of fabrics, e.g., clothes, and plants such as flowers or trees. It is clear that the precursors of the invention can also be used to release active compounds, notably fragrances, from liquids, like in liquid air-fresheners or air-freshening devices in the form of gels.

Of course, the above examples are only illustrative and non-limiting as they relate to preferred embodiments. All other current articles or products in functional and fine perfumery may contain the precursors of the present invention, and these articles or products include soaps, bath or shower gels, cosmetic preparations, body deodorants, and even perfumes or colognes.

In the above-cited applications, the precursor of the present invention can be used alone, in mixture with other precursors, and/or with other active ingredients such as perfuming ingredients, solvents and adjuvants of current use in the art. The nature and variety of these co-ingredients do not require a detailed description which, moreover could not be exhaustive, and a person skilled in the art is able to choose said co-ingredients by his general knowledge and in function of the nature of the product to be treated and the generated effect sought. These perfuming co-ingredients belong to such varied chemical classes as alcohols, aldehydes, ketones, esters, ethers, acetates, nitrites, terpene hydrocarbons, nitrogen- or sulphur-containing heterocyclic compounds, as well as essential oils of natural or synthetic origin. By way of example, embodiments of compounds can be found in standard reference works, such as the book of S. Arctander, Perfume and Flavour Chemicals, 1969, Montclair, N.J., USA, or more recent versions thereof, or in other works of similar nature.

The proportions in which the compound of formula (I) can be incorporated in the various above-mentioned consumer products vary within a wide range of values. These values depend on the nature of the active compound to be released, the nature of the article or product which has to be prepared and the desired generated effect, as well as on the nature of the co-ingredients in a given composition when the compounds of the present invention are used in admixture with perfuming, masking, antimicrobial, insect repelling or attracting co-ingredients, solvents or adjuvants of current use in the art.

By way of example, one can cite typical concentrations of the order of 0.01 to 5%, or even 10% by weight relative to the weight of the consumer products cited above into which it is incorporated. Higher concentrations than those mentioned above can be used when, in particular, a fragrance precursor is applied in perfuming compositions, perfumes or colognes.

Several methods can be employed for the preparation of compounds of formula (I). One route for the preparation of these compounds (I) wherein Y represents a phenyl group starts with the esterification of an oxo-phenyl acid with sulphuric acid in methanol, followed by protection of the carbonyl function with ethylene glycol. The intermediate ketal (A) can be reduced with $LiAlH_4$ in ether to obtain an alcohol which is esterified under dicyclohexylcarbodiimide (DCC) coupling conditions. Deprotonation of the ketal with hydrochloric acid in tetrahydrofuran (THF) finally affords a series of phenyl ketones of formula (I) in a five step sequence.

Moreover, saponification of the same intermediate (A) with LiOH and treatment with methyllithium affords a carbonyl compound which can be further derived. For example, a Grignard-type reaction with 5-bromo-2-methyl-2-pentene, followed by acetalization of the tertiary alcohol function and deprotection of the carbonyl protecting group affords another phenyl ketone according to formula (I).

An alternative route used for the preparation of a series of phenyl ketones as well as for the preparation of pyridyl ketones starts from oxo-phenyl chlorides, respectively oxo-pyridyl chlorides. In a first step, the carbonyl function is protected with ethylene glycol. Etherification with an alcoholate in tetrahydrofuran, followed by deprotection of the carbonyl function leads to further series of compounds which can be expressed by formula (I) in a three steps sequence.

Schemes 1 and 2 below illustrate the general preparation of these compounds:

or alkylene group from $C_1$ to $C_{20}$, an unsubstituted or substituted mono- or poly-cycloalkyl group from $C_3$ to $C_8$,

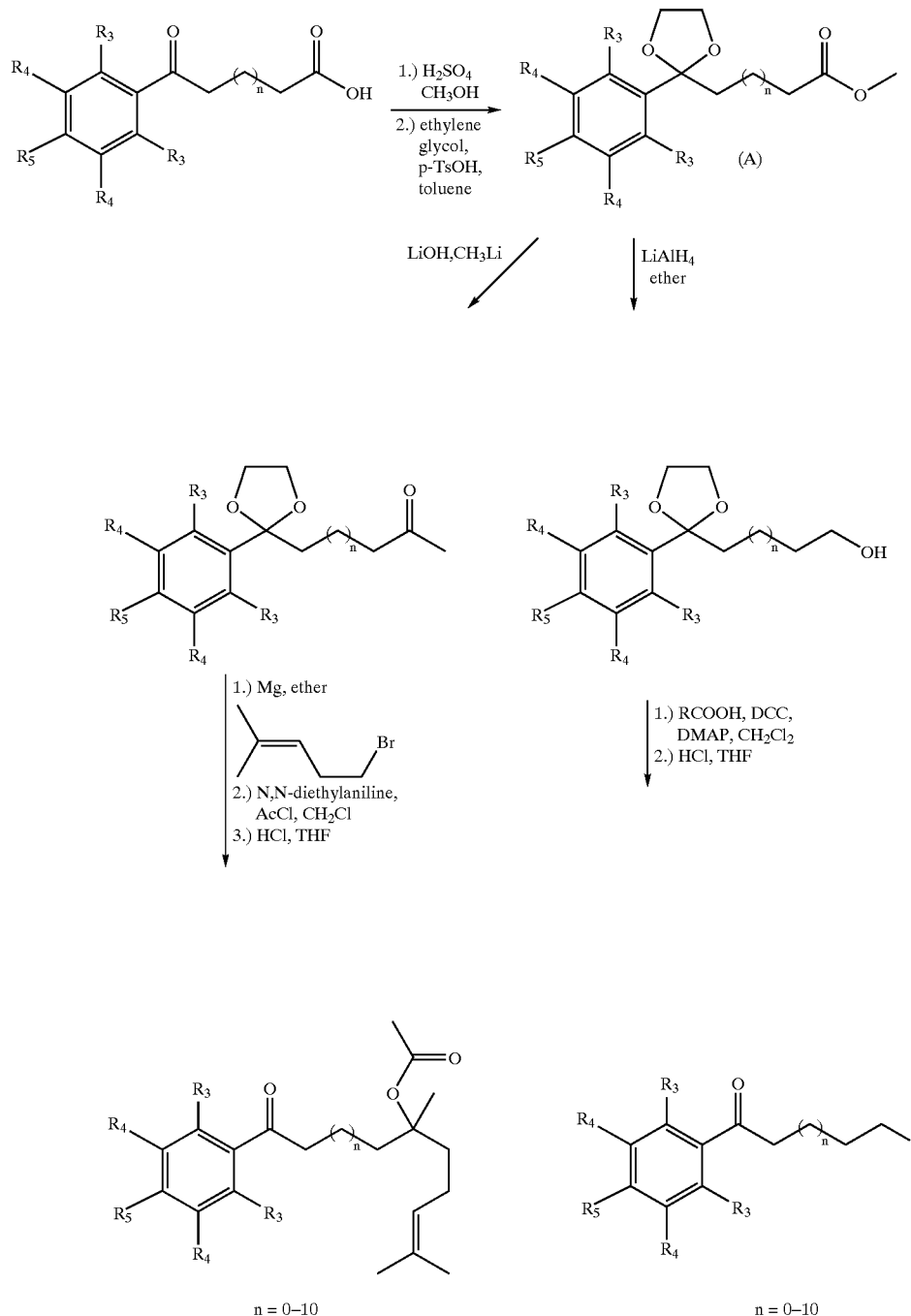

wherein $R_3$, $R_4$, $R_5$ have the same meaning as in formula (I) and R represents a hydrogen atom, a linear or branched alkyl or an unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulfur.

Scheme 2

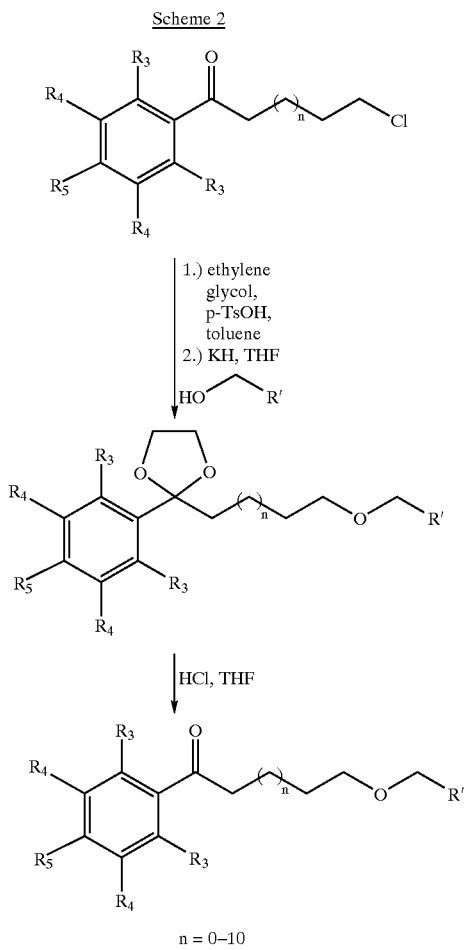

n = 0–10 wherein $R_3$, $R_4$, $R_5$ have the same meaning as in formula (I) and R' represents a hydrogen atom, a linear or branched alkyl or alkylene group from $C_1$ to $C_{20}$, an unsubstituted or substituted mono- or poly-cycloalkyl group from $C_3$ to $C_8$, or an unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulfur. The reagents that were used are as follows:

p-TsOH: p-toluenesulfonic acid
DCC: dicyclohexylcarbodiimide
DMAP: 4-dimethylaminopyridine
AcCl: acetyl chloride

EXAMPLES

The invention will now be described in greater detail in the following examples in which the temperatures are indicated in degrees centigrade and the abbreviations have the usual meaning in the art.

General

Commercially available reagents and solvents were used without further purification if not stated otherwise. The following chemicals were obtained from commercial sources: 5-oxo-5-phenylpentanoic acid, sulfuric acid, p-toluenesulfonic acid, lithium aluminum hydride, dicyclohexylcarbodiimide (DCC), 4-dimethylaminopyridine (DMAP), heptanoic acid, hydrochloric acid, 3-cyclohexylpropanoic acid, phenoxyacetic acid, 1,4-diphenyl-1-butanoate, methyl lithium, lithium hydroxide, N,N-diethylaniline, acetyl chloride, 4-chloro-1-(4-methylphenyl)-1-butanone, 4-chloro-1-(4-methoxyphenyl)-1-butanone, 1-(4-tert-butylphenyl)-4-chloro-1-butanone, 2-phenylethanol, decanol and potassium hydride. Reactions were carried out in standard glassware under $N_2$ if not stated otherwise. 5-Bromo-2-methyl-2-pentane was prepared from 1-cyclopropyl-1-ethanone in an analogous manner to the method described by Biemacki and Gdula in Synthesis, 1979,-37–38

Example 1

Preparation of Substituted and Unsubstituted Phenyl Ketones

1. Preparation of 5-oxo-5-phenylpentyl heptanoate
a) Synthesis of methyl 5-oxo-5-phenylpentanoate A solution of 50.0 g of 5-oxo-5-phenylpentanoic acid (260 mmol) (origin: Fluka) and 70 ml of conc. $H_2SO_4$ in 1400 ml of methanol was heated under reflux for 1 h. The reaction mixture was cooled down to room temperature and added to 2 l of water and extracted with ether (2×). The organic phase was washed with water (1×), an aq. solution of $NaHCO_3$ (10%, 2×), again with water (2×), dried ($Na_2SO_4$) and concentrated to give 47.9 g (90%) of a slightly yellow oil, which slowly crystallizes at 4° C.

Analytical data:
UV/Vis (hexane): 369 (sh, 2), 355 (sh, 12), 339 (sh, 33), 322 (45), 309 (sh, 41), 287 (600), 278 (800), 248 (sh, 7900), 238 (13200).
IR (neat): 3061w, 3022w, 2949m, 2902w, 1730s, 1681s, 1597m, 1580m, 1447m, 1435m, 1412m, 1370m, 1315m, 1277m, 1254m, 1207s, 1174s, 1146s, 1073m, 1055m, 1013m, 1000m, 990m, 975m, 931w, 879m, 843w, 739s, 689s, 657w.
$^1$H-NMR (360 MHz, $CDCl_3$): 8.02–7.92 (m, 2H); 7.59–7.52 (m, 1H); 7.50–7.41 (m, 2H); 3.68 (s, 3H); 3.05 (t, J=7.1, 2H); 2.45 (t, J=7.3, 2H); 2.08 (quint., J=7.2, 2H).
$^{13}$C-NMR (90.6 MHz, $CDCl_3$): 199.35 (s); 173.69 (s); 136.82 (s); 133.08 (d); 128.60 (d); 128.02 (d); 51.56 (q); 37.44 (t); 33.11 (t); 19.34(t).
MS (EI): 206 (M$^+$, 7), 175 (10), 174 (3), 147 (8), 146 (8), 133 (3), 120 (14), 106 (8), 105 (100), 78 (3), 77 (35), 59 (3), 55 (5), 51 (10).

b) Synthesis of methyl 4-(2-phenyl-1,3-dioxolan-2-yl) butanoate

A solution of 47.9 g (230 mmol) of methyl 5-oxo-5-phenylpentanoate obtained under a), 45 ml of ethylene glycol and ≈1 g of p-toluenesulfonic acid was heated for 23 h under reflux with azeotropic removal of water. After cooling down to room temperature, the reaction mixture was extracted with ether (2×), washed with a sat. aq. solution of $NaHCO_3$ (2×), water (2×) and a sat. aq. solution of NaCl. The organic phase was dried ($Na_2SO_4$) and concentrated to give 63.1 g (100%) of a colorless oil, containing 2-hydroxyethyl 4-(2-phenyl-1,3-dioxolan-2-yl) butanoate (a) in addition to methyl 4-(2-phenyl-1,3-dioxolan-2-yl) butanoate (b).

Analytical data for (a):
IR (neat): 3447m (br.), 2948m, 2918w, 2885m, 1730s, 1487m, 1472w, 1446m, 1416w, 1382m, 1346m, 1307w, 1290w, 1257m, 1218m, 1166s, 1075m, 1038s, 1026s, 947s, 904w, 882m, 841w, 826w, 765m, 702s, 654m.

$^1$H-NMR (360 MHz, CDCl$_3$): 7.47–7.40 (m, 2H); 7.37–7.25 (m, 3H); 4.22–4.15 (m, 2H); 4.06–3.96 (m, 2H); 3.83–3.71 (m, 4H); 2.40 (t, J=6.1, 1H); 2.35 (t, J=7.3, 2H); 1.97–1.89 (m, 2H); 1.78–1.66 (m, 2H).

$^{13}$C-NMR (90.6 MHz, CDCl$_3$): 173.67 (s); 142.27 (s); 128.16 (d); 127.93 (d); 125.63 (d); 110.11 (s); 65.93 (t); 64.49 (t); 61.13 (t); 39.53 (t); 33.96 (t); 19.10 (t).

MS (EI): 219 (7), 203 (3), 150 (11), 149 (100), 105 (24), 99 (8), 55 (3).

Analytical data for (b):

UV/Vis (hexane): 287 (sh, 18), 280 (sh, 21), 271 (sh, 30), 266 (sh, 70 (weak)), 263 (160), 256 (200), 250 (190), 245 (180), 240 (180), 235 (sh, 160), 215 (sh, 4700), 210 (sh, 8600), 205 (10000).

IR (neat): 2949m, 2918w, 2885m, 1733s, 1489w, 1473w, 1446m, 1435m, 1363w, 1309w, 1290w, 1257m, 1217m, 1189s, 1165s, 1086w, 1069m, 1039s, 1027s, 990m, 947m, 919m, 879w, 851w, 827w, 764m, 701s, 654m.

$^1$H-NMR (360 MHz, CDCl$_3$): 7.47–7.40 (m, 2H); 7.37–7.23 (m, 3H); 4.06–3.94 (m, 2H); 3.81.3.71 (m, 2H); 3.63 (s, 3H); 2.30 (t, J=7.5, 2H); 1.96–1.87 (m, 2H); 1.75–1.63 (m, 2H).

$^{13}$C-NMR (90.6 MHz, CDCl$_3$): 173.90 (s); 142.41 (s); 128.12 (d); 127.86 (d); 125.68 (d); 110.10 (s); 64.51 (t); 51.42 (q); 39.69 (t); 33.92 (t); 19.17 (t).

MS (EI): 219 (5), 173 (4), 150 (10), 149 (100), 105 (30), 99 (8), 77 (11).

c) Synthesis of 4-(2-phenyl-1,3-dioxolan-2-yl)-1-butanol

A solution of 63.1 g of the mixture obtained under b) in 350 ml of ether was added dropwise during 3 h at 0° C. under N$_2$, to a suspension of 9.6 g (250 mmol) of LiAlH$_4$ in 350 ml of ether. After the introduction, the reaction mixture was left heating up to room temperature and then brought to reflux for 3 h. After cooling down to 0° C., 5 ml of a sat. aq. solution of Na$_2$SO$_4$ were added and the formation of a precipitate was observed. The reaction mixture was filtered and the organic phase dried over Na$_2$SO$_4$ and concentrated to give 47.6 g (86%) of a slightly yellow oil.

Analytical data:

UV/Vis (hexane): 286 (sh, 15), 271 (sh, 24), 267 (sh, 50 (weak)), 263 (140), 257 (170), 251 (140), 245 (sh, 90), 240 (sh, 66), 235 (sh, 46), 215 (sh, 4000), 211 (8000), 206 (9500).

IR (neat): 3353m (br.), 2943m, 2916m, 2878m, 1489w, 1473w, 1458w, 1447m, 1342w, 1310w, 1275w, 1231m, 1207m, 1186m, 1155m, 1070m, 1041s, 1026m, 1000m, 967m, 945m, 906m, 875m, 764m, 701s.

$^1$H-NMR (360 MHz, CDCl$_3$): 7.48–7.41 (m, 2H); 7.38–7.24 (m, 3H); 4.06–3.95 (m, 2H); 3.82–3.71 (m, 2H); 3.59 (t, J=5.5, 2H); 1.97–1.88 (m, 2H); 1.59–1.48 (m, 3H); (1.48–1.35 (m, 2H).

$^{13}$C-NMR (90.6 MHz, CDCl$_3$): 142.50 (s); 128.09 (d); 127.81 (d); 125.70 (d); 110.38 (s); 64.48 (t); 62.73 (t); 40.13 (t); 32.67 (t); 19.83 (t).

MS (EI): 150 (10), 149 (100), 145 (3), 106 (3), 105 (36), 91 (3), 77 (16), 55 (3), 51 (4), 31 (3)

d) Synthesis of 4-(2-phenyl-1,3-dioxolan-2-yl)butyl heptanoate

A solution of 1.66 g of heptanoic acid (12.7 mmol), 0.15 g (1.3 mmol) of DMAP (4-dimethylaminopyridine) and 5.00 g (23.0 mmol) of 4-(2-phenyl-1,3-dioxolan-2-yl)-1-butanol obtained under c) in 30 ml of dichloromethane was cooled on an ice-bath, before a solution of 3.00 g (14.8 mmol) of DCC (dicyclohexylcarbodiimide) in 16 ml of dichloromethane was added during 15 min. The reaction mixture was stirred for 10 min at 0° C., then at room temperature for 4 h. The precipitate formed in the reaction was filtered off and the filtrate taken up in ether, washed with water (3×), HCl (10%, 3×), and a sat. solution of Na$_2$CO$_3$ (3×). The organic layer was dried (Na$_2$SO$_4$), concentrated and chromatographed (SiO$_2$, heptane/ether 8:2) to give 3.15 g (74%) of a colourless oil.

Analytical data:

R$_f$ (heptane/ether 8:2): 0.32.

UV/Vis (hexane): 286 (sh, 28), 278 (sh, 35), 271 (sh, 50), 267 (sh, 85), 263 (180), 256 (230), 250 (220), 245 (240), 240 (240).

IR (neat): 2951m, 2926m, 2871m, 1732s, 1488w, 1458m, 1447m, 1421w, 1390w, 1377w, 1348w, 1309w, 1296m, 1276m, 1233m, 1211m, 1163s, 1101m, 1043s, 1026s, 970m, 945m, 918m, 898m, 886m, 764m, 701s.

$^1$H-NMR (360 MHz, CDCl$_3$): 7.47–7.40 (m, 2H); 7.37–7.24 (m, 3H); 4.06–3.94 (m, 4H); 3.82–3.70 (m, 2H); 2.25 (t, J=7.5, 2H); 1.96–1.86 (m, 2H); 1.67–1.51 (m 4H); 1.47–1.20 (m, 8H); 0.88 (t, J=6.7, 3H).

$^{13}$C-NMR (90.6 MHz, CDCl$_3$): 173.92 (s); 142.49 (s); 128.08 (d); 127.80 (d); 125.69 (d); 110.27 (s); 64.49 (t), 64.16 (t); 40.09 (t); 34.36 (t); 31.46 (t); 28.82 (t); 28.65 (t); 24.94 (t); 22.48 (t); 20.14 (t); 14.04 (q).

MS (EI): 150 (10), 149 (100), 143 (3), 105 (21), 77 (8), 55 (3), 43 (8), 41 (4), 29 (3).

e) Synthesis of 5-oxo-5-phenylpentyl heptanoate 2.32 ml of a 1N solution of HCl were added to a solution of 4.37 g (13.0 mmol) of 4-(2-phenyl-1,3-dioxolan-2-yl) butyl heptanoate obtained under d) in 18 ml of THF (tetrahydrofuran). The reaction mixture was heated to 40° C. for 24 h, cooled down to room temperature, extracted with ethyl acetate (2×) and washed with a sat. solution of NaCl (3×). The organic phase was dried (Na$_2$SO$_4$) and concentrated. Column chromatography (SiO$_2$, heptane/ether 8:2) afforded 2.74 g (73%) of a colourless oil, which crystallises at 4° C.

Analytical data:

R$_f$ (heptane/ether 8:2): 0.28.

UV/Vis (hexane): 373 (sh, 2), 354 (sh, 14), 339 (sh, 32), 323 (44), 310 (sh, 40) 286 (1000), 277 (1200), 247 (sh, 7700), 239 (12600).

IR (neat): 3059w, 2952m, 2928m, 2857m, 1730s, 1685s, 1597m, 1580m, 1448m, 1413w, 1376m, 1356m, 1322w, 1297w, 1257m, 1232m, 1202m, 1166s, 1101m, 1076w, 1058w, 1026w, 1101m, 979m, 888w, 752m, 732m, 689s, 654m.

$^1$H-NMR (360 MHz, CDCl$_3$): 7.99–7.92 (m, 2H); 7.60–7.51 (m, 1H); 7.50–7.41 (m, 2H); 4.12 (t, J=6.3, 2H); 3.02 (t, J=6.9, 2H); 2.29 (t, J=7.7, 2H); 1.88–1.68 (m, 4H); 1.65–1.55 (m, 2H); 1.38–1.22 (m, 6H); 0.88 (t, J=6.7, 3H).

$^{13}$C-NMR (90.6 MHz, CDCl$_3$): 173.95 (s); 136.93 (s); 133.03 (d); 128.60 (d); 128.01 (d); 63.90 (t); 37.89 (t); 34.36 (t); 31.45 (t); 28.83 (t); 28.24 (t); 24.96 (t); 22.48 (t); 20.65 (t); 14.02 (q).

MS (EI): 177 (5), 161 (12), 160 (21), 120 (4), 106 (7), 105 (100), 77 (18), 55 (4), 51 (3), 43 (10), 51 (5), 29 (3).

2. Preparation of 5-oxo-5-phenylpentyl 3-cyclohexylpropionate a) Synthesis of 4-(2-phenyl-1,3-dioxolan-2-yl)butyl 3-cyclohexylpropionate This compound was synthesised as described under 1.d) with 1.98 g (12.7 mmol) of 3-cyclopropionic acid for 3 h. Column chromatography (SiO$_2$, heptane/ether 1:1->ether) gave 4.12 g (90%) of a slightly yellow oil.

Analytical data:

R$_f$ (heptane/ether 1:1): 0.59.

UV/Vis (hexane): 295 (sh, 40), 287 (sh, 100), 262 (510), 256 (550), 251 (500), 245 (sh, 450), 241 (sh, 400), 227 (sh, 530).

IR (neat): 2920s, 2849m, 1732s, 1489w, 1447m, 1390w, 1354w, 1348w, 1309m, 1292w, 1274m, 1250m, 1209m, 1162s, 1123m, 1075m, 1043s, 1026m, 969m, 946m, 917w, 888m, 841w, 764m, 701s.

$^1$H-NMR (360 MHz, CDCl$_3$): 7.47–7.40 (m, 2H); 7.37–7.23 (m, 3H); 4.07–3.94 (m, 4H); 3.82–3.72 (m, 2H); 2.31–2.22 (m, 2H); 1.96–1.86 (m, 2H); 1.76–1.35 (m, 11H); 1.33–1.05 (m, 4H); 0.96–0.79 (m, 3H).

$^{13}$C-NMR (90.6 MHz, CDCl$_3$): 174.21 (s); 142.49 (s); 128.08 (d); 127.80 (d); 125.69 (d); 110.26 (s); 64.49 (t); 64.18 (t); 40.09 (t); 37.23 (d); 32.96 (t); 32.35 (t); 31.93 (t); 28.64 (t); 26.55 (t); 26.23 (t); 20.15 (t).

MS (EI): 161 (4), 150 (10), 149 (100), 145 (3), 143 (3), 105 (19), 77 (7), 55 (7), 41 (4).

b) Synthesis of 5-oxo-5-phenylpentyl 3-cyclohexylpropionate

This compound was synthesised as described under 1.e) with 2.0 ml of a 1N solution of HCl, 4.12 g (11.4 mmol) of 4-(2-phenyl-1,3-dioxolan-2-yl)butyl 3-cyclohexylpropionate obtained under a) in 20 ml of THF for 19 h. Column chromatography (SiO$_2$, heptane/ether 3:2) afforded 2.15 g (60%) of a yellow oil containing small amounts of impurities, which can be distilled off (Kugelrohr, 150° C./1×10$^2$ Pa).

Analytical data:

R$_f$ (heptane/ether 8:2): 0.29.

UV/Vis (hexane): 370 (sh, 3), 355 (sh, 13), 337 (sh, 35), 322 (45), 311 (sh, 42), 287 (750), 278 (980), 272 (sh, 920), 247 (sh, 8100), 238 (12600).

IR (neat): 2920s, 2845m, 1729s, 1684s, 1596m, 1579m, 1447m, 1413m, 1392m, 1356m, 1322m, 1308m, 1293m, 1274m, 1250m, 1228m, 1202m, 1178s, 1162s, 1123m, 1077m, 1060w, 1027w, 1000m, 969m, 885m, 842m, 786w, 752m, 732m, 689s, 654m.

$^1$H-NMR (360 MHz, CDCl$_3$): 8.00–7.92 (m, 2H); 7.61–7.52 (m, 1H); 7.51–7.42 (m, 2H); 4.12 (t, J=6.3, 2H); 3.06–2.97 (m, 2H); 2.34–2.25 (m, 2H); 1.91–1.58 (m, 9H); 1.57–1.46 (m, 2H); 1.30–1.05 (m, 4H); 0.96–0.80 (m, 2H).

$^{13}$C-NMR (90.6 MHz, CDCl$_3$): 199.76 (s); 174.25 (s); 136.93 (s); 133.03 (d); 128.60 (d); 128.01 (d); 63.93 (t); 37.90 (t); 37.24 (d); 32.96 (t); 32.37 (t); 31.93 (t); 28.22 (t); 26.53 (t); 26.22 (t); 20.65 (t).

MS (EI): 177 (6), 162 (5), 161 826), 160 (32), 138 (4), 133 (3), 121 (4), 120 (5), 106 (8), 105 (100), 95 (3), 77 (17), 69 (3), 67 (3), 55 (10), 41 (7).

3. Preparation of 5-oxo-5-phenylpentyl phenoxyacetate a) Synthesis of 4-(2-phenyl-1,3-dioxolan-2-yl) butylphenoxyacetate This compound was synthesised as described under 1.d) with 1.93 g (12.7 mmol) of phenoxyacetic acid. Column Chromatography (SiO$_2$, heptane/ether 1:1->2:8) gave 3.58 g (79%) of a slightly yellow solid.

Analytical data:

R$_f$ (heptane/ether 1:1): 0.48.

UV/Vis (hexane): 276 (1500), 270 (1800), 263 (1400), 257 (sh, 890), 250 (sh, 510), 244 (sh, 360).

IR (neat): 3059w, 3027w, 2951m, 2914m, 2885m, 1756s, 1732m, 1598m, 1588m, 1493s, 1456w, 1446m, 1394w, 1371w, 1335w, 1307m, 1286m, 1273m, 1185s, 1172s, 1086s, 1072s, 969m, 946m, 916w, 883m, 839w, 818w, 786m, 752s, 702s, 689s.

$^1$H-NMR (360 MHz, CDCl$_3$): 7.47–7.40 (m, 2H); 7.38–7.22 (m, 5H); 7.03–6.94 (m, 1H); 6.93–6.84 (m, 2H); 4.58 (s, 2H); 4.15 (t, J=6.7, 2H); 4.05–3.93 (m, 2H) 3.82–3.70 (m, 2H); 1.96–1.86 (m, 2H); 1.69–1.57 (m, 2H); 1.47–1.34 (m, 2H).

$^{13}$C-NMR (90.6 MHz, CDCl$_3$): 168.98 (s); 157.82 (s); 142.42 (s); 129.54 (d); 128.11 (d); 127.84 (d); 125.68 (d); 121.69 (d); 114.66 (d); 110.18 (s); 65.33 (t); 65.23 (t); 64.49 (t); 39.97 (t); 28.48 (t); 20.01 (t).

MS (EI): 150 (10), 149 (100), 107 (4), 105 (21), 77 (15), 51 (3).

b) Synthesis of 5-oxo-5-phenylpentyl phenoxyacetate

This compound was synthesised as described under 1.e) with 1.45 ml of a 1N solution of HCl, 2.90 g (8.1 mmol) of 4-(2-phenyl-1,3-dioxolan-2-yl)butyl phenoxyacetate obtained under a) in 13 ml of THF for 17 h. Column chromatography (SiO$_2$, heptane/ether 8:2) afforded 1.98 g (78%) of a slightly yellow oil.

Analytical data:

R$_f$ (heptane/ether 8:2): 0.09.

UV/Vis (hexane): 371 (sh, 1), 355 (sh, 8), 337 (sh, 24), 321 (32), 310 (sh, 31), 286 (540), 277 (1800), 270 (1900), 263 (sh, 1400), 247 (sh, 6600), 238 (10300), 223 (sh, 8500), 219 (8900).

IR (neat): 3061w, 3031w, 2951m, 1754s, 1732m, 1681s, 1597s, 1587m, 1493s, 1447m, 1409w, 1394w, 1372w, 1357w, 1334w, 1286m, 1270m, 1230m, 1191s, 1172s, 1026m, 1000m, 974m, 884m, 836w, 817w, 785m, 751s, 734m, 688s.

$^1$H-NMR (360 MHz, CDCl$_3$): 7.99–7.91 (m, 2H); 7.60–7.52 (m, 1H); 7.50–7.42 (m, 2H); 7.34–7.23 (m, 2H); 7.05–6.84 (m, 3H); 4.62 (s, 2H); 4.26 (t, J=6.1, 2H) 2.99 (t, J=6.7, 2H); 1.86–1.69 (m, 2H).

$^{13}$C-NMR (90.6 MHz, CDCl$_3$): 199.63 (s); 169.08 (s); 157.79 (s); 136.87 (s); 133.08 (d); 129.56 (d); 128.62 (d); 128.00 (d); 121.73 (d); 114.63 (d); 65.32 (t); 65.01 (t); 37.73 (t); 28.07 (t); 20.42 (t).

MS (EI): 312 (M$^+$, 7), 162 (9), 161 (76), 152 (9), 107 (12), 106 (8), 105 (100), 79 (6), 78 (5), 77 (45), 55 (4), 51 (10), 39 (3)

4. Preparation of 1,5-dimethyl-1-(4-oxo-4-phenylbutyl)-4-hexenyl acetate a) Synthesis of 4-(2-phenyl-1,3-dioxolan-2-yl)butanoic acid A solution of 1.06 g (0.044 mol) of LiOH in 40 ml of water was added during 10 min to 10.0 g (0.04 mol) of methyl 4-(2-phenyl-1,3-dioxolan-2-yl)butanoate obtained under 1.b) in 200 ml of water. The reaction mixture was left stirring for 2.5 h and quenched with 30 ml of HCl (5%). Extraction with ethyl acetate (4×), drying (Na$_2$SO$_4$) and concentrating gave 8.76 g (93%) of a slightly yellow solid.

Analytical data:

IR (neat): 3054m, 2956m, 2915m, 2885m, 2767w, 2697w, 2632w, 1734m, 1689s, 1674s, 1596m, 1580m, 1480w, 1461m, 1445m, 1431m, 1412m, 1376m, 1349w, 1333w, 1319w, 1307m, 1288m, 1270m, 1231m, 1210m, 1184s, 1155w, 1144m, 1087m, 1072m, 1065m, 1054m, 1038m, 1025m, 1000m, 971m, 944m, 936s, 918m, 858w, 841m, 772m, 759m, 734m, 781m, 691s, 659m.

$^1$H-NMR (360 MHz, CDCl$_3$): 7.47–7.40 (m, 2H); 7.37–7.23 (m, 3H); 4.05–3.96 (m, 2H); 3.80–3.71 (m, 2H); 2.39–2.27 (m 2H); 1.98–1.87 (m, 2H); 1.77–1.63 (m, 2H).

$^{13}$C-NMR (90.6 MHz, CDCl$_3$): 179.39 (s); 142.32 (s); 128.14 (d); 127.89 (d); 125.65 (d); 110.08 (s); 64.49 (t); 39.50 (t); 33.82 (t); 18.86 (t).

MS (EI): 175 (13), 174 (3), 150 (4), 149 (30), 147 (11), 146 (12), 120 (10), 106 (9), 105 (100), 91 (4), 86 (4), 78 (5), 77 (41), 55 (8), 51 (12), 45 (5), 43 (3), 42 (7), 41 (4), 39 (3).

b) Synthesis of 5-(2-phenyl-1,3-dioxolan-2-yl)-2-pentanone

A well stirred solution of 5.0 g (0.021 mol) of 4-(2-phenyl-1,3-dioxolan-2-yl)butanoic acid obtained under a) in 50 ml of THF was cooled down to 0° before 12.5 ml of methyl lithium (1.69M, 1 eq.) were added during 1 h. The mixture took up in mass and 30 ml of THF were added to get a white solution. The reaction mixture was left stirring for 30 min while warming up to room temperature. Another 25 ml of methyl lithium (2 eq.) were added during 2 h to give a yellow solution, which was poured onto ice. The THF was evaporated and the crude reaction mixture taken up in ether, washed with a saturated solution of NaCl, dried ($Na_2SO_4$) and concentrated. Column chromatography ($SiO_2$, heptane/ether 3:2) gave 2.36 g (48%) of 5-(2-phenyl-1,3-dioxolan-2-yl)-2-pentanone (a) and 1.50 g (29%) of 2-methyl-5-(2-phenyl-1,3-dioxolan-2-yl)-2-pentanol (b) as yellow oils.

Analytical data for (a):

$R_f$ (heptane/ether 3:2): 0.25.

UV/Vis (hexane): 287 (sh, 370), 276 (sh, 540), 267 (sh, 610), 263 (670), 256 (660), 250 (sh, 640), 246 (660), 240 (660), 225 (sh, 580).

IR (neat): 3058w, 3025w, 2955m, 2918m, 2885m, 1711s, 1668w, 1600w, 1487w, 1480w, 1446m, 1410m, 1357m, 1305m, 1284w, 1254m, 1231w, 1217m, 1187m, 1161m, 1072m, 1040s, 1026s, 974m, 946m, 908m, 852w, 762m, 736w, 701s.

$^1$H-NMR (360 MHz, $CDCl_3$): 7.48–7.39 (m, 2H); 7.38–7.24 (m, 3H); 4.07–3.95 (m, 2H); 3.82–3.70 (m, 2H); 2.41 (t, J=7.5, 2H); 2.09 (s, 3H); 1.93–1.84 (m, 2H); 1.73–1.58 (m, 2H).

$^{13}$C-NMR (90.6 MHz, $CDCl_3$): 208.79 (s); 142.40 (s); 128.12 (d); 127.86 (d); 125.67 (d); 110.17 (s); 64.49 (t); 43.52 (t); 39.62(t); 29.81 (q); 18.03 (t).

MS (EI): 150 (10), 149 (100), 105 (31), 99 (6), 77 (13), 51 (3), 43 (8).

Analytical data for (b):

$R_f$ (heptane/ether 3:2): 0.09.

UV/Vis (hexane): 295 (sh, 47), 287 (sh, 120), 279 (sh, 190), 270 (sh, 250), 263 (370), 257 (410), 245 (sh, 720), 238 (840), 228 (sh, 720).

IR (neat): 3412m (br.), 3060w, 3025w, 2960m, 2916w, 2881m, 1711w, 1684w, 1598w, 1581w, 1488w, 1468w, 1446m, 1371m, 1294m, 1259m, 1213m, 1181m, 1152m, 1076w, 1038s, 1025s, 990m, 971m, 947m, 914s, 824w, 813w, 756m, 736w, 700s.

$^1$H-NMR (360 MHz, $CDCl_3$): 7.48–7.41 (m, 2H); 7.37–7.24 (m, 3H); 4.07–3.95 (m, 2H); 3.82–3.70 (m, 2H); 3.95–1.84 (m, 2H), 1.49–1.36 (m, 4H); 1.17 (s, 6H)

$^{13}$C-NMR (90.6 MHz, $CDCl_3$): 142.61 (s); 128.08 (d); 127.78 (d); 125.69 (d); 110.39 (s); 70.94 (s); 64.46 (t); 43.81 (t); 40.86 (t); 29.19 (q); 18.43 (t).

MS (EI): 173 (3), 150 (10), 149 (100), 133 (4), 121 (5), 105 (24), 77 (11), 59 (4), 43 (5).

c) Synthesis of 4,8-dimethyl-1-(2-phenyl-1, 3-dioxolan-2-yl)-7-nonen-4-ol

A Grignard reagent of 3.50 g (0.021 mol) of 5-bromo-2-methyl-2-pentene in 13 ml of ether and 0.62 g (0.026 mol) of magnesium turnings in 14 ml of ether was added slowly at −25° under $N_2$ to a stirred solution of 5.54 g (0.024 mol) of 5-(2-phenyl-1,3-dioxolan-2-yl)-2-pentanone obtained under b) in 20 ml of ether. During the introduction, the temperature was left rising up to −5° C. and the reaction mixture left stirring for 45 min. Then a saturated solution of $NH_4Cl$ was added and the formation of a white precipitate was observed. Extraction with ether (2×), washing with water (3×), drying ($Na_2SO_4$) and concentrating gave 6.24 g of the crude product. Column chromatography ($SiO_2$, heptane/ether 7:3) gave 2.53 g (38%) of a yellow oil.

Analytical data:

$R_f$ (heptane/ether 7:3): 0.12

IR (neat): 3433m (br.), 3059w, 3025w, 2958m, 2915m, 2881m, 1488w, 1445m, 1373m, 1337w, 1308w, 1291w, 1255w, 1214m, 1182m, 1116m, 1075w, 1038s, 1025s, 972m, 945m, 914m, 840w, 809w, 759m, 701s.

$^1$H-NMR (360 MHz, $CDCl_3$): 7.48–7.41 (m, 2H); 7.37–7.24 (m, 3H); 5.14–5.06 (m, 1H); 4.07–3.95 (m, 2H); 3.82–3.71 (m, 2H); 2.06–1.94 (m, 2H); 1.94–1.85 (m, 2 H); 1.67 (s, 3H); 1.59 (s, 3H); 1.47–1.34 (m, 6H); 1.12 (s, 3H).

$^{13}$C-NMR (90.6 MHz, $CDCl_3$): 142.63 (s); 131.65 (s); 128.08 (d); 127.77 (d); 125.69 (d); 124.49 (d); 110.38 (s); 72.74 (s); 64.47 (t); 41.89 (t); 41.57 (t); 40.92 (t); 26.71 (q); 25.70 (q); 22.63 (t); 18.01 (t); 17.63 (q).

MS (EI): 318 ($M^+$, 0.1), 150 (9), 149 (100), 147 (4), 142 (9), 134 (3), 133 (7), 121 (10), 109 (4), 105 (30), 99 (3), 93 (3), 91 (3), 77 (11), 71 (4), 69 (9), 67 (3), 58 (3), 55 (7), 43 (13), 41 (13).

d) Synthesis of 1,5-dimethyl-1-[3-(2-phenyl-1,3-dioxolan-2-yl)propyl]-4-hexenyl acetate A stirred solution of 2.38 g (7.5 mmol) of 4,8-dimethyl-1-(2-phenyl-1,3-dioxolan-2-yl)-7-nonen-4-ol obtained under c), 3.34 g (22 mmol) of N,N-diethylaniline, 1.75 g (22 mmol) of acetyl chloride in 150 ml of $CH_2Cl_2$ was heated under reflux for 3 days. Another equivalent of N,N-diethyl aniline (1.1 g, 7.3 mmol) and acetyl chloride (0.6 g, 7.3 mmol), respectively, were added after 24, 48, 65 and 71 h. The reaction mixture was cooled down to room temperature, acidified with 2M HCl, extracted with ether (2×), washed with a saturated solution of $NaHCO_3$ (2×), dried ($Na_2SO_4$) and concentrated. Column chromatography ($SiO_2$, heptane/ether 4:1) gave 2.04 g (76%) of a yellow oil.

Analytical data:

$R_f$ (heptane/ether 4:1): 0.17

IR (neat): 2960m, 2917m, 2879m, 2851w, 1727s, 1488w, 1463w, 1447m, 1375m, 1365m, 1342w, 1303w, 1243s, 1216m, 1186m, 1154m, 1112m, 1075m, 1038s, 1026s, 973m, 947m, 931m, 873w, 833w, 761m, 702s, 654w.

$^1$H-NMR (360 MHz, $CDCl_3$): 7.48–7.39 (m, 2H); 7.38–7.24 (m, 3H); 5.11–5.01 (m, 1H); 4.07–3.94 (m, 2H); 3.82–3.70 (m, 2H); 1.98–1.75 (m, 6H); 1.92 (s, 3H) 1.75–1.52 (m, 2H); 1.66 (s, 3H); 1.57 (s, 3H); 1.44–1.14 (m, 2H); 1.36 (s, 3 H).

$^{13}$C-NMR (90.6 MHz, $CDCl_3$): 170.33 (s); 142.59 (s); 131.58 (s); 128.06 (d); 127.76 (d); 125.69 (d); 124.02 (d); 110.35 (s); 84.54 (s); 64.47 (t); 40.61 (t); 38.25 (t); 38.07 (t); 25.68 (q); 23.68 (q); 22.34 (t, q); 17.78 (t); 17.54 (q).

MS (EI): 238 (10), 169 (3), 150 (10), 149 (100), 142 (5), 136 (5), 133 (3), 121 (12), 105 (31), 99 (4), 93 (7), 91 (3), 77 (10), 69 (6), 43 (4), 41 (5).

e) Synthesis of 1,5-dimethyl-1-(4-oxo-4-phenylbutyl)-4-hexenyl acetate 1.76 ml of HCl (1N) was added slowly to a solution of 1.63 g (4.53 mmol) of 1,5-dimethyl-1-[3-(2-phenyl-1,3-dioxolan-2-yl)propyl]-4-hexenyl acetate obtained under d) in 30 ml of THF. The reaction mixture was stirred at 40° or 4 h, cooled down to room temperature, extracted with ether, washed with a saturated solution of NaCl (3×), dried ($Na_2SO_4$), filtered and concentrated. Column chromatography ($SiO_2$, heptane/ether 4:1) yielded 1.34 g (94%) of a slightly yellow oil.

Analytical data:

$R_f$ (heptane/ether 4:1): 0.29

UV/Vis (hexane): 370 (sh, 4), 356 (sh, 14), 341 (sh, 34), 322 (52), 311 (52), 287 (1400), 279 (sh, 1600), 246 (sh, 10000), 239 (13000).

IR (neat): 2962m, 2921m, 2878m, 2853m, 1725s, 1684s, 1597m, 1580m, 1467w, 1448m, 1408w, 1364m, 1304w, 1272m, 1246s, 1204m, 1178m, 1158m, 1109m, 1089m, 1065w, 1045w, 1016m, 1001m, 978m, 938m, 888w, 829w, 794w, 751m, 732m, 690s, 656w.

¹H-NMR (360 MHz, CDCl₃): 7.99–7.91 (m, 2H); 7.60–7.52 (m, 1H); 7.51–7.41 (m, 2 H); 5.15–5.05 (m, 1H); 2.98 (t, J=7.1, 2H); 2.05–1.55 (m, 8H); 1.97 (s, 3 H); 1.68 (s, 3H); 1.60 (s, 3H); 1.45 (s, 3H).
¹³C-NMR (90.6 MHz, CDCl₃): 199.96 (s); 170.44 (s); 136.98 (s); 132.99 (d); 131.70 (s); 128.59 (d); 128.00 (d); 123.93 (d); 84.42 (s); 38.65 (t); 38.24 (t); 37.81 (t); 25.69 (q); 23.71 (q); 22.36 (t, q); 18.39 (t); 17.58 (q).
MS (EI): 257 (3), 256 (14), 241 (3), 238 (6), 223 (4), 214 (3), 213 (17), 195 (3), 188 (3), 187 (14), 174 (9), 173 (5), 172 (3), 171 (21), 169 (3), 151 (3), 147 (9), 145 (3), 137 (6), 136 (48), 134 (8), 133 (30), 131 (3), 123 (3), 122 (3), 121 (24), 120 (26), 119 (3), 115 (3), 110 (3), 109 (37), 107 (9), 106 (9), 105 (100), 95 (4), 94 (6), 93 (41), 92 (9), 91 (9), 82 (6), 81 (7), 80 (8), 79 (5), 78 (5), 77 (31), 69 (23), 67 (8), 60 (3), 55 (6), 53 (3), 51 (3), 43 (9), 41 (10).

5. Preparation of 4-(decyloxy)-1-(4-methoxyphenyl)-1-butanone a) Synthesis of 2-(3-chloropropyl)-2-(4-methoxyphenyl)-1,3-dioxolane A solution of 20.0 g (94.0 mmol) of 4-chloro-1-(4-methoxyphenyl)-1-butanone (origin: Acros), 19 ml of ethylene glycol and ca. 1 g of p-toluenesulfonic acid in 120 ml of toluene was heated under reflux with azeotropic removal of water for 16 h. After cooling down to room temperature, ether was added and the organic phase extracted with a saturated solution of NaHCO₃ (2×), washed with water (2×), dried (Na₂SO₄) and concentrated in vacuo to give 24.6 g (99%) of the crude compound, which was used for further functionalization. Column chromatography of 2 g (SiO₂, heptane/ether 9:1) afforded 1.15 g of a slightly yellow oil.

Analytical data:

$R_f$ (heptane/ether 9:1): 0.25

IR (neat): 2956m, 2882m, 2831m, 1610m, 1583m, 1508m, 1463m, 1442m, 1412w, 1372w, 1347w, 1300m, 1239s, 1169s, 1142m, 1108m, 1079w, 1030s, 1009m, 946m, 907m, 855w, 830s, 814m, 800m, 781w, 764w, 746w, 722w.

¹H-NMR (360 MHz, CDCl₃): 7.39–7.32 (m, 2H); 6.91–6.83 (m, 2H); 4.06–3.94 (m, 2H); 3.84–3.71 (m, 2H); 3.80 (s, 3H); 3.52 (t, J=6.7, 2H); 2.06–1.97 (m, 2H) 1.91–1.79 (m, 2H).

¹³C-NMR (90.6 MHz, CDCl₃): 159.34 (s); 134.38 (s); 126.92 (d); 113.49 (d); 109.95 (s); 64.47 (t); 55.25 (q); 45.16 (t); 37.85 (t); 27.16 (t).

MS (EI): 256 (M⁺, 0.4), 180 (18), 179 (100), 149 (4), 136 (7), 135 (68), 121 (3), 107 (6), 92 (7), 77 (8).

b) Synthesis of 2-[3-(decyloxy)propyl]-2-(4-methoxyphenyl)-1,3-dioxolane 13.80 g of potassium hydride (30% in oil, 0.1 mol) were washed with pentane (3×) and THF (3×). Then, 75 ml of THF were added and the suspension was heated to reflux before a solution of 11.70 g (74 mmol) of decanol in 19 ml of THF was added during 5–10 min. After keeping at reflux for 2.5 h, a solution of 19.00 g (74 mmol) of 2-(3-chloropropyl)-2-(4-methoxyphenyl)-1,3-dioxolane obtained under a) in 19 ml of THF was added during 15 min and the reaction mixture left stirring under reflux for 65 h. After cooling down to room temperature, the excess of KH was quenched by adding dropwise ca. 10 ml of water. The reaction mixture was concentrated, taken up in dichloromethane, extracted with water and HCl (10%), washed with water, dried (Na₂SO₄) and concentrated to give 24.19 g of the crude compound. Column chromatography of 10 g (SiO₂, heptane/ether 9:1) afforded 2.71 g (23%) of a yellowish oil.

Analytical data:

$R_f$ (heptane/ether 9:1): 0.15

IR (neat): 2921m, 2851m, 2795w, 1664w, 1610m, 1581w, 1510m, 1484w, 1464m, 1442m, 1418w, 1377w, 1381w, 1301m, 1244s, 1196m, 1168s, 1110s, 1033s, 1010m, 989m, 952m, 831s, 811m, 801m, 754w, 738w, 720w, 694w, 662w.

¹H-NMR (360 MHz, CDCl₃): 7.40–7.32 (m, 2H); 6.90–6.81 (m, 2H); 4.07–3.95 (m, 2H); 3.84–3.70 (m, 2H); 3.80 (s, 3H); 3.36 (t, J=6.9, 2H); 3.34 (t, J=6.9, 2H); 1.97–1.88 (m, 2H); 1.71–1.57 (m, 2H); 1.57–1.46 (m, 2H); 1.38–1.17 (m, 14H); 0.88 (t, J=6.9, 3H).

¹³C-NMR (90.6 MHz, CDCl₃): 159.21 (s); 134.73 (s); 127.00 (d); 113.36 (d); 110.33 (s); 70.87 (t); 70.71 (t); 64.46 (t); 55.23 (q); 37.18 (t); 31.92 (t); 29.76 (t); 29.63 (t); 29.60 (t); 29.52 (t); 29.35 (t); 26.19 (t); 24.14 (t); 22.70 (t); 14.13 (q).

MS (EI): 181 (4), 180 (35), 179 (100), 177 (12), 163 (3), 151 (4), 150 (11), 136 (7), 135 (63), 121 (5), 113 (3), 107 (6), 92 (4), 77 (5), 69 (3), 57 (3), 55 (3), 43 (5), 41 (4).

c) Synthesis of 4-(decyloxy)-1-(4-methoxyphenyl)-1-butanone 3 ml of HCl (1N) were added to a solution of 2.64 g (6.9 mmol) of 2-[3-(decyloxy)propyl]-2-(4-methoxyphenyl)-1,3-dioxolane obtained under b) in 50 ml of THF. The reaction mixture was heated at 40° for 2 h. After cooling down to room temperature, ether was added and the reaction mixture washed with a saturated solution of NaCl (3×). The organic phase was dried (Na₂SO₄) and concentrated to give 2.29 g (99%) of a slightly red oil that solidifies at 4°.

Analytical data:

UV/Vis (hexane): 398 (sh, 3), 379 (sh, 7), 362 (sh, 15), 346 (sh, 47), 332 (sh, 90), 318 (sh, 120), 298 (sh, 900), 277 (sh, 17700), 271 (sh, 24700), 262 (31300), 220 (sh, 19900), 213 (27700).

IR (neat): 3052w, 2952w, 2928m, 2915m, 2849m, 2802w, 1667s, 1593s, 1510m, 1491w, 1469m, 1456m, 1444m, 1414w, 1374m, 1356m, 1342m, 1312m, 1281w, 1260s, 1243m, 1234w, 1213m, 1188w, 1170s, 1132w, 1111s, 1073w, 1060w, 1025m, 1012m, 990m, 964m, 921m, 889w, 879w, 854w, 835s, 815m, 800w, 786w, 757m, 739w, 720m, 668w.

¹H-NMR (360 MHz, CDCl₃): 7.99–7.91 (m, 2H); 6.99–6.88 (m, 2H); 3.86 (s, 3H); 3.49 (t, J=6.1, 2H); 3.40 (t, J=6.7, 2H); 3.02 (t, J=7.1, 2H); 2.06–1.95 (m, 2H); 1.61–1.49 (m, 2H); 1.38–1.17 (m, 14H); 0.88 (t, J=6.7, 3H).

¹³C-NMR (90.6 MHz, CDCl₃): 198.69 (s); 163.36 (s); 130.32 (d); 130.22 (s); 113.65 (d); 70.98 (t); 69.84 (t); 55.42 (q); 34.82 (t); 31.92 (t); 29.77 (t); 29.64 (t); 29.60 (t); 29.53 (t); 29.35 (t); 26.23 (t); 24.55 (t); 22.70 (t); 14.12 (q).

MS (EI): 177 (4), 151 (10), 150 (100), 136 (3), 135 (31), 92 (3), 77 (4), 43 (3).

6. Preparation of 1-(4-methoxyphenyl)-4-(2-phenylethoxy)-1-butanone a) Synthesis of 2-(4-methoxyphenyl)-2-[3-(2-phenylethoxy)propyl]-1,3-dioxolane This compound was synthesized as described under 5.b) with 2.00 g of potassium hydride (30% in oil, 15.0 mmol) in 10 ml of THF, 1.40 g (11.5 mmol) of 2-phenylethanol in 3 ml of THF and 3.0 g (11.7 mmol) of 2-(3-chloropropyl)-2-(4-methoxyphenyl)-1,3-dioxolane obtained under 5.a) in 3 ml of THF. Column chromatography (SiO₂, heptane/ether 4:1) afforded 1.21 g (31%) of a yellow oil.

Analytical data:

$R_f$ (heptane/ether 4:1): 0.17

IR (neat): 3061w, 3023w, 2944m, 2856m, 2791w, 1662w, 1609m, 1581m, 1508m, 1495m, 1463m, 1452m, 1442m, 1412w, 1359m, 1300m, 1243s, 1191m, 1168m, 1109s, 1030s, 1011w, 977w, 951m, 907w, 830s, 814w, 802w, 748m, 731w, 698s, 663w.

$^1$H-NMR (360 MHz, CDCl$_3$): 7.38–7.32 (m, 2H); 7.31–7.23 (m, 2H); 7.22–7.15 (m, 3H); 6.88–6.82 (m, 2H); 4.04–3.93 (m, 2H); 3.82–3.70 (m, 2H); 3.80 (s, 3H); 3.57 (t, J=7.3, 2H); 3.40 (t, J=6.7, 2H); 2.84 (t, J=7.3, 2H); 1.95–1.88 (m, 2H); 1.68–1.57 (m, 2H).

$^{13}$C-NMR (90.6 MHz, CDCl$_3$): 159.21 (s); 139.10 (s); 134.68 (s); 128.90 (d); 128.29 (d); 126.99 (d); 126.10 (d); 113.38 (d); 110.30 (s); 71.68 (t); 70.82 (t); 64.46 (t); 55.25 (q); 37.10 (t); 36.35 (t); 24.08 (t).

MS (EI): 180 (11), 179 (100), 135 (19), 105 (4), 91 (3), 77 (3).

b) Synthesis of 1-(4-methoxyphenyl)-4-(2-phenylethoxy)-1-butanone

This compound was synthesized as described under 5.c) with 0.8 ml of HCl (1N) and 0.65 g (1.9 mmol) of 2-(4-methoxyphenyl)-2-[3-(2-phenylethoxy)propyl]-1,3-dioxolane obtained under a) in 50 ml of THF. Column chromatography (SiO$_2$, heptane/ether 4:1) gave 0.44 g (78%) of white crystals.

Analytical data:

R$_f$ (heptane/ether 4:1): 0.13

UV/Vis (hexane): 361 (sh, 5), 345 (sh, 35), 331 (sh, 78), 315 (110), 306 (110), 277 (sh, 9800), 270 (sh, 14800), 264 (18400), 220 (sh, 10800), 212 (19400).

IR (neat): 3062w, 3051w, 3026w, 3001w, 2955m, 2936m, 2900m, 2864m, 2802w, 1669s, 1833w, 1595s, 1535w, 1511m, 1493m, 1486m, 1469m, 1464m, 1451m, 1438w, 1410m, 1377w, 1362s, 1310s, 1276w, 1255s, 1211s, 1174s, 1147m, 1120m, 1111s, 1096s, 1086m, 1068w, 1046w, 1027m, 1014s, 1008m, 977s, 912w, 908w, 875w, 938s, 926s, 816m, 796w, 766m, 749s, 720w, 698s.

$^1$H-NMR (360 MHz, CDCl$_3$): 7.96–7.87 (m, 2H); 7.31–7.14 (m, 5H); 6.95–6.87 (m, 2H); 3.85 (s, 3H); 3.63 (t, J=7.1, 2H); 3.51 (t, J=5.9, 2H); 2.96 (t, J=7.1, 2 H); 2.87 (t, J=7.1, 2H); 1.99 (quint, J=6.6, 2H).

$^{13}$C-NMR (90.6 MHz, CDCl$_3$): 198.66 (s); 163.34 (s); 139.13 (s); 130.32 (d); 130.17 (s); 128.92 (d); 128.30 (d); 126.13 (d); 71.63 (t); 69.89 (t); 55.44 (q); 36.34 (t); 34.72 (t); 24.45 (t).

MS (EI): 178 (3), 177 (20), 151 (10), 150 (100), 136 (5), 135 (57), 121 (4), 107 (5), 105 (6), 104 (3), 92 (7), 91 (6), 79 (3), 77 (11).

7. Preparation of 4-(decyloxy)-1-(4-methylphenyl)-1-butanone a) Synthesis of 2-(3-chloropropyl)-2-(4-methylphenyl)-1,3-dioxolane This compound was synthesized as described under 5.a) with 20.0 g (101.6 mmol) of 4-chloro-1-(4-methylphenyl)-1-butanone (origin: Acros), 20 ml of ethylene glycol and ca. 1 g of p-toluenesulfonic acid in 120 ml of toluene to give 25.2 g (99%) of the crude compound, which was used for further functionalization. Column chromatography of 2 g (SiO$_2$, heptane/ether 9:1) afforded 1.51 g of a yellow oil.

Analytical data:

R$_f$ (heptane/ether 9:1): 0.33

IR (neat): 3023w, 2956m, 2918m, 2882m, 1910w, 1683m, 1607m, 1573w, 1509m, 1471m, 1403m, 1374m, 1300w, 1307m, 1300m, 1287m, 1230m, 1179s, 1141m, 1110m, 1081w, 1038s, 1018s, 945s, 908s, 856w, 815s, 780m, 746w, 719m.

$^1$H-NMR (360 MHz, CDCl$_3$): 7.32 (d, J=8.3, 2H); 7.14 (d, J=7.9, 2H); 4.05–3.93 (m, 2H); 3.82–3.70 (m, 2H); 3.51 (t, J=6.7, 2H); 2.34 (s, 3H); 2.06–1.97 (m, 2H); 1.91–1.79 (m, 2H).

$^{13}$C-NMR (90.6 MHz, CDCl$_3$): 139.28 (s); 137.63 (s); 128.87 (d); 125.59 (d); 110.03 (s); 64.48 (t); 45.15 (t); 37.79 (t); 27.12 (t); 21.11 (q).

MS (EI): 195 (3), 164 (24), 163 (100), 151 (4), 149 (12), 128 (3), 120 (8), 119 (74), 117 84), 115 (6), 105 (7), 91 (25), 90 (3), 89 (4), 65 (5).

b) Synthesis of 2-[3-(decyloxy)propyl]-2-(4-methylphenyl)-1,3-dioxolane

This compound was synthesized as described under 5.b) with 14.90 g of potassium hydride (30% in oil, 0.11 mol) in 80 ml of THF, 13.10 g (82.7 mmol) of decanol in 20 ml of THF and of 20.00 g (83.0 mmol) of 2-(3-chloropropyl)-2-(4-methylphenyl)-1,3-dioxolane obtained under a) in 20 ml of THF for 41 h to give 29.49 g of the crude compound. Repetitive column chromatography of ca. 10 g batches (SiO$_2$, heptane/ether 9:1) afforded a total of 5.05 g (17%) of a yellow oil.

Analytical data:

R$_f$ (heptane/ether 9:1): 0.21.

IR (neat): 2952m, 2922s, 2851s, 2795w, 1685m, 1626w, 1606m, 1573w, 1509m, 1465m, 1455m, 1405w, 1375m, 1359m, 1298m, 1255m, 1224m, 1196m, 1179m, 1112s, 1042s, 1019m, 991m, 953m, 897w, 840w, 818s, 772w, 724m, 662w.

$^1$H-NMR (360 MHz, CDCl$_3$): 7.33 (d, J=7.9, 2H); 7.13 (d, J=7.9, 2H); 4.04–3.93 (m, 2H); 3.82–3.70 (m, 2H); 3.36 (t, J=7.5, 2H); 3.33 (t, J=6.7, 2H); 2.33 (s, 3H); 1.96–1.89 (m, 2H); 1.69–1.58 (m, 2H); 1.58–1.46 (m, 2H); 1.36–1.19 (m, 14H); 0.88 (t, J=6.9, 3H).

$^{13}$C-NMR (90.6 MHz, CDCl$_3$): 139.62 (s); 137.36 (s); 128.74 (d); 125.69 (d); 110.42 (s); 70.86 (t); 70.72 (t); 64.47 (t); 37.14 (t); 31.92 (t); 29.77 (t); 29.60 (t, 2×); 29.53 (t); 29.36 (t); 26.20 (t); 24.10 (t); 22.70 (t); 21.10 (q); 14.13 (q).

MS (EI): 271 (5), 164 (30), 163 (100), 161 (8), 135 (8), 134 (3), 120 (4), 119 (46), 113 (4), 105 (3), 91 (12).

c) Synthesis of 4-(decyloxy)-1-(4-methylphenyl)-1-butanone

This compound was synthesized as described under 5.c) with 4.4 ml of HCl (1N) and 4.33 g (11.9 mmol) of 2-[3-(decyloxy)propyl]-2-(4-methylphenyl)-1,3-dioxolane obtained under b) in 100 ml of THF to give 3.82 g (99%) of a slightly yellow oil that solidifies at 4°.

Analytical data:

UV/Vis (hexane): 400 (sh, 2), 381 (sh, 6), 365 (sh, 12), 352 (sh, 26), 336 (sh, 51), 320 (64), 308 (sh, 62), 288 (sh, 1200), 277 (sh, 2400), 254 (sh, 14300), 248 (17400), 211 (sh, 16400).

IR (neat): 3032w, 2921s, 2851s, 2792w, 1682s, 1624w, 1606m, 1573w, 1484w, 1466m, 1454m, 1443m, 1408m, 1380m, 1319m, 1293m, 1268m, 1251m, 1238m, 1224m, 1204m, 1179m, 1111s, 1036m, 1018w, 1001m, 983m, 965w, 916w, 898w, 839w, 806m, 776m, 757m, 721m, 664w.

$^1$H-NMR (360 MHz, CDCl$_3$): 7.87 (d, J=7.9, 2H); 7.24 (d, J=7.9, 2H); 3.49 (t, J=6.3, 2H); 3.39 (t, J=6.5, 2H); 3.04 (t, J=7.1, 2H); 2.39 (s, 3H); 2.01 (quint, J=6.6, 2H); 1.63–1.48 (m, 2H); 1.38–1.17 (m, 14H); 0.88 (t, J=6.9, 3H).

$^{13}$C-NMR (90.6 MHz, CDCl$_3$): 199.67 (s); 143.59 (s); 134.66 (s); 129.21 (d); 128.19 (d); 70.99 (t); 69.81 (t); 35.06 (t); 31.94 (t); 29.79 (t); 29.67 (t); 29.62 (t); 29.55 (t); 29.38 (t); 26.25 (t); 24.46 (t); 22.72 (t); 21.60 (q); 14.13 (q).

MS (EI): 318 (M$^+$, 3), 185 (8), 183 (4), 161 (10), 147 (6), 135 (16), 134 (100), 120 (5), 119 (54), 92 (4), 91 (18), 65 (3).

8. Preparation of 1-(4-methylphenyl)-4-(2-phenylethoxy)-1-butanone a) Synthesis of 2-(4-methylphenyl)-2-[3-(2-phenylethoxy)propyl]-1,3-dioxolane This compound was synthesized as described under 5.b) with 3.1 g of potassium hydride (30% in oil, 23.2 mmol) in 10 ml of THF, 2.1 g (17.2 mmol) of 2-phenylethanol in 4 ml of THF and 4.0 g (16.6 mmol) of 2-(3-chloropropyl)-2-(4-methylphenyl)-1,3-dioxolane obtained under 7.a) in 4 ml of THF for 68 h. Column chromatography (SiO$_2$, heptane/ether 4:1) afforded 2.64 g (49%) of a slightly yellow oil.

Analytical data:

R$_f$ (heptane/ether 4:1): 0.31.

IR (neat): 3085w, 3058w, 3022w, 2948m, 2916m, 2855m, 2790w, 2731w, 1604w, 1510m, 1494m, 1472w, 1452m, 1405w, 1359m, 1303m, 1254m, 1225m, 1192m, 1179m, 1166m, 1109s, 1037s, 951s, 907w, 844w, 817s, 770w, 748m, 724m, 698s, 665w.

$^1$H-NMR (360 MHz, CDCl$_3$): 7.36–7.22 (m, 4H); 7.22–7.10 (m, 5H); 4.05–3.93 (m, 2H); 3.82–3.70 (m, 2H); 3.56 (t, J=7.3, 2H); 3.40 (t, J=6.7, 2H); 2.84 (t, J=7.3, 2H); 2.34 (s, 3H); 1.96–1.87 (m, 2H); 1.69–1.57 (m, 2H).

$^{13}$C-NMR (90.6 MHz, CDCl$_3$): 139.56 (s); 139.09 (s); 137.42 (s); 128.90 (d); 128.75 (d); 128.29 (d); 126.10 (d); 125.68 (d); 110.38 (s); 71.67 (t); 70.83 (t); 64.48 (t); 37.05 (t); 36.35 (t); 24.02 (t); 21.11 (q).

MS (EI): 235 (8), 165 (4), 164 (51), 163 (50), 161 (26), 147 (3), 145 (3), 135 (8), 134 (3), 133 (3), 131 (4), 129 (3), 128 (3), 120 (11), 119 (100), 118 (4), 117 86), 115 (7), 113 (8), 106 (3), 105 (34), 104 (4), 103 (8), 92 (6), 91 (56), 90 (5), 89 (4), 79 (8), 78 (3), 77 (9), 69 (3), 65 (10).

b) Synthesis of 1-(4-methylphenyl)-4-(2-phenylethoxy)-1-butanone

This compound was synthesized as described under 5.c) with 2.3 ml of HCl (1N), 2.05 g (6.3 mmol) of 2-(4-methylphenyl)-2-[3-(phenylethoxy)propyl]-1,3-dioxolane obtained under a) in 50 ml of THF for 3 h to give 1.81 g (99%) of a slightly yellow oil that solidifies at 4° C.

Analytical data:

UV/Vis (hexane): 352 (sh, 18), 336 (sh, 43), 318 (59), 308 (58), 287 (sh, 800), 276 (sh, 1200), 256 (sh, 9800), 246 (14800).

IR (neat): 3082w, 3060w, 3025w, 2921m, 2855m, 2790w, 1679s, 1605m, 1571w, 1494m, 1484w, 1452m, 1439w, 1407m, 1359m, 1317m, 1276w, 1250m, 1239w, 1219w, 1202m, 1179m, 1108s, 1029m, 1001m, 981m, 900w, 842w, 807m, 769w, 747m, 698s, 858w.

$^1$H-NMR (360 MHz, CDCl$_3$): 7.83 (d, J=8.3, 2H); 7.30–7.14 (m, 7H); 3.63 (t, J=7.1, 2H); 3.52 (t, J=6.1, 2H); 2.98 (t, J=7.1, 2H); 2.86 (t, J=7.1, 2H); 2.40 (s, 3H); 2.05–1.94 (m, 2H).

$^{13}$C-NMR (90.6 MHz, CDCl$_3$): 199.71 (s); 143.63 (s); 139.11 (s); 134.58 (s); 129.19 (d); 128.92 (d); 128.29 (d); 128.19 (d); 126.13 (d); 71.64 (t); 69.87 (t); 36.33 (t); 34.98 (t); 24.33 (t); 21.62 (q).

MS (EI): 191 (3), 177 (4), 162 (7), 161 (57), 160 (3), 149 (6), 147 (4), 135 (10), 134 (100), 120 (8), 119 (90), 106 (3), 105 (25), 104 (41), 103 (5), 92 (7), 91 (48 ), 90 (3), 89 (4), 79 (6), 77 (7), 65 (12), 39 (3).

9. Preparation of 1-(4-tert-butylphenyl)-4-(2-phenylethoxy)-1-butanone a) Synthesis of 2-(4-tert-butylphenyl)-2-(3-chloropropyl)-1,3-dioxolane This compound was synthesized as described under 5.a) with 20.0 g (83.8 mmol) of 1-(4-tert-butylphenyl)-4-chloro-1-butanone (origin: Acros), 16 ml of ethylene glycol and ca. 1 g of p-toluenesulfonic acid in 120 ml of toluene for 16 h to give 24.1 g (99%) of the crude compound, which was used for further functionalization. Column chromatography of 3 g (SiO$_2$, heptane/ether 4:1) afforded 2.48 g of a slightly yellow oil.

Analytical data:

R$_f$ (heptane/ether 4:1): 0.49.

IR (neat): 2958m, 2883m, 1915w, 1684w, 1610w, 1505m, 1473m, 1460m, 1443m, 1397m, 1362m, 1310m, 1300m, 1288m, 1267m, 1235m, 1186s, 1149w, 1107m, 1080w, 1039s, 1017s, 945s, 909s, 857w, 829s, 783w, 762w, 744w, 734w, 713w.

$^1$H-NMR (360 MHz, CDCl$_3$): 7.35 (s, 4H); 4.05–3.95 (m, 2H); 3.84–3.73 (m, 2H); 3.53 (t, J=6.7, 2H); 2.06–1.99 (m, 2H); 1.91–1.81 (m, 2H); 1.32 (s, 9H).

$^{13}$C-NMR (90.6 MHz, CDCl$_3$): 150.80 (s); 139.23 (s); 125.27 (d); 125.05 (d); 110.03 (s); 64.55 (t); 45.21 (t); 37.79 (t); 34.50 (s); 31.36 (q); 27.09 (t).

MS (EI): 206 (23), 205 (100), 195 (4), 190 (9), 189 (3), 162 (3), 161 (30), 149 (4), 146 (4), 145 (4), 131 (4), 118 (6), 117 (4), 115 (5), 105 (3), 91 (4).

b) Synthesis of 2-(4-tert-butylphenylyl)-2-[3-(2-phenylethoxy)propyl]-1,3-dioxolane This compound was synthesized as described under 5.b) with 1.30 g of potassium hydride (30% in oil, 9.7 mmol) in 5 ml of THF, 0.86 g (7.0 mmol) of 2-phenylethanol in 2 ml of THF and 2.0 g (7.1 mmol) of 2-(4-tert-butylphenyl)-2-(3-chloropropyl)-1,3-dioxolane obtained under a) in 2 ml of THF for 90 h. Column chromatography (SiO$_2$, heptane/ether 4:1) afforded 1.04 g (40%) of a white solid.

Analytical data:

IR (neat): 2947m, 2920m, 2882m, 2861m, 2794w, 1604w, 1508w, 1496m, 1480m, 1466m, 1454m, 1446m, 1432w, 1413w, 1396m, 1360m, 1305m, 1290m, 1265m, 1237m, 1191w, 1167m, 1133w, 1102s, 1080m, 1040s, 1016s, 1002w, 984s, 956s, 945s, 912m, 880s, 846m, 833s, 776w, 754s, 715w, 704s, 680w.

$^1$H-NMR (360 MHz, CDCl$_3$): 7.38–7.30 (m, 4H); 7.30–7.22 (m, 2H); 7.22–7.14 (m, 3H); 4.05–3.92 (m, 2H); 3.85–3.72 (m, 2H); 3.57 (t, J=7.1, 2H); 3.40 (t, J=6.7, 2H); 2.84 (t, J=7.3, 2H); 1.98–1.87 (m, 2H); 1.71–1.57 (m, 2H); 1.31 (s, 9H).

$^{13}$C-NMR (90.6 MHz, CDCl$_3$): 150.57 (s); 139.48 (s); 139.07 (s); 128.89 (d); 128.28 (d); 126.09 (d); 125.35 (d); 124.92 (d); 110.37 (s); 71.70 (t); 70.87 (t); 64.53 (t); 37.03 (t); 36.35 (t); 34.48 (s); 31.37 (q); 24.04 (t).

MS (EI): 206 (16), 205 (100), 203 (3), 161 (11), 118 (3), 105 (5), 91 (5).

c) Synthesis of 1-(4-tert-butylphenyl)-4-(2-phenylethoxy)-1-butanone

This compound was synthesized as described under 5.c) with 2 ml of HCl (1N) and 2.00 g (5.4 mmol) of 2-(4-tert-butylphenyl)-2-[3-(2-phenylethoxy)propyl]-1,3-dioxolane obtained under b) in 50 ml of THF to give 1.77 g (99%) of a yellow oil.

Analytical data:

UV/Vis (hexane): 352 (sh, 21), 333 (sh, 54), 321 (64), 308 (sh, 62), 287 (sh, 900), 277 (sh, 1400), 258 (sh, 10900), 248 (17800).

IR (neat): 3085w, 3060w, 3026w, 2957m, 2930m, 2904m, 2861m, 2795w, 1679s, 1604m, 1585w, 1494m, 1474m, 1463m, 1452m, 1440m, 1405m, 1361m, 1320m, 1295m, 1268m, 1249m, 1212m, 1190m, 1158w, 1106s, 1030m, 997m, 923w, 901w, 840m, 825m, 767m, 747m, 734m, 697s.

$^1$H-NMR (360 MHz, CDCl$_3$): 7.92–7.84 (m, 2H); 7.50–7.42 (m, 2H); 7.30–7.14 (m, 5H); 3.63 (t, J=6.9, 2H); 3.51 (t, J=6.1, 2H); 3.00 (t, J=7.1, 2H); 2.86 (t, J=6.9, 2H); 2.00 (quint., J=6.6, 2H); 1.34 (s, 9H).

$^{13}$C-NMR (90.6 MHz, CDCl$_3$): 199.71 (s); 156.56 (s); 139.10 (s); 134.48 (s); 128.90 (d); 128.29 (d); 128.03 (d); 126.11 (d); 125.44 (d); 71.64 (t); 69.85 (t); 36.32 (t); 35.06 (s); 34.95 (t); 31.10 (q); 24.34 (t).

MS (EI): 219 (3), 204 (8), 203 (51), 188 (3), 187 (5), 177 (12), 176 (88), 162 (13), 161 (100), 147 (4), 146 (9), 145 (6), 133 (4), 132 (4), 131 (3), 118 (12), 117 (8), 115 (5), 105 (20), 104 (25), 103 (5), 91 (15), 79 (4), 77 (6).

Example 2

Release of Fragrant Terminal Alkenes After Irradiation of Different Phenyl Ketones in Solution

Execution of Photorelease Assays and Analysis of Phenyl Ketones

Photorelease Assays

The photorelease assays were carried out in undegassed solution with either a Xenon lamp (Heraeus Suntest CPS at 460 W/m$^2$) or outdoor sunlight (Geneva, spring 2000), respectively, and quantified by GC. Ca. 0.08 M solutions of the different phenyl ketones in the indicated solvent were prepared by adding 1 ml of a 0.01 M solution of dodecane (which was used as an internal standard for the GC analysis) to 5 ml of a 0.01 M solution of the phenyl ketone. Three samples of these solutions were then irradiated during 3 h in 10 ml borosilicate volumetric glass flasks (Pyrex®). In each case a dark control experiment (an additional sample being wrapped in aluminum foil) was carried out. The identity of the products formed was systematically verified based on GC retention times and GC-MS analyses of the irradiated samples.

Analysis

GC analyses were carried out on a Carlo Erba MFC 500 chromatograph equipped with a Fisons AS 800 autosampler, a flame ionization detector and a J&W Scientific DB1 capillary column (15 m, 0.32 mm i.d.) at 70° for 10 min then to 260° (10° C./min), helium pressure 50 kPa, injection volume 0.5 µl, injection temperature 250°, detector temperature 260°. GC-MS analyses were carried out on a HP 5890 or 6890 GC System equipped with a Supelco SPB-1 capillary column (30 m, 0.25 mm i.d.) at 70° for 10 min then to 260° (10°/min), helium flow ca 1 ml/min, coupled with a HP MSD 5972 or 5973 quadrupole mass spectrometer, electron energy ca 70 eV, fragment ions m/z (rel. int. in % of the base peak).

The release of 1,5-dimethyl-1-vinyl-4-hexenyl acetate, decylvinyl ether, 2-phenylethyl-vinyl ether, allyl heptanoate, allyl 3-cyclohexylpropionate, allyl phenoxyacetate and vinylbenzene as well as the corresponding acetophenone residues from phenyl ketones precursors was investigated by photoirradiation in solution, as described above. Table 1 reports the yields of compounds released in mol-%:

TABLE 1

Results of the photoirradiations of different phenyl ketones in solution

| Irradiated Compound of Formula (I) | Number | Light Source | Toluene 3 h (Acetophenone) | Toluene 3 h (Alkene) | 2-Propanol 3 h (Acetophenone) | 2-Propanol 3 h (Alkene) | Acetonitrile 3 h (Acetophenone) | Acetonitrile 3 h (Alkene) |
|---|---|---|---|---|---|---|---|---|
| (Ph-CO-CH₂CH₂CH₂-Ph) | 1 | Xenon / sunlight |  |  | 61 / n.d.$^a$) | 41 / 32 | 49 / n.d. | 55 / 43 |
| (diketone with O-linker) | 2 | Xenon / sunlight | 71 / n.d. | 68 / 80 | 26 / 32 | 36 / 41 | 48 / 44 | 72 / 66 |
| (diketone with cyclohexyl-O) | 3 | Xenon / sunlight | 72 / n.d. | 66 / 76 | 23 / 29 | 31 / 37 | 41 / 33 | 68 / 62 |
| (diketone with phenoxy-O) | 4 | Xenon / sunlight | 64 | 55 | 24 / 26 | 15 / 19 | 51 / 47 | 64 / 60 |

TABLE 1-continued

Results of the photoirradiations of different phenyl ketones in solution

| Irradiated Compound of Formula (I) | Number | Light Source | Yield of Corresponding Alkenes and Acetophenones Released [mol %] | | | | | |
|---|---|---|---|---|---|---|---|---|
| | | | Toluene 3 h | | 2-Propanol 3 h | | Acetonitrile 3 h | |
| | | | Acetophenone | Alkene | Acetophenone | Alkene | Acetophenone | Alkene |
|  | 5 | Xenon sunlight | 62 69 | 54 53 | 32 | 57 | 40 54 | 46 40 |
|  | 6 | Xenon sunlight | 28 30 | 21 25 | 30 | 31 | 25 54 | 26 35 |
|  | 7 | Xenon sunlight | 31 39 | 35 38 | n.d. | 64 | 34 35 | 48 38 |
|  | 8 | Xenon sunlight | 26 35 | 32 38 | | | 21 22[b] | 32 48[b] |
| 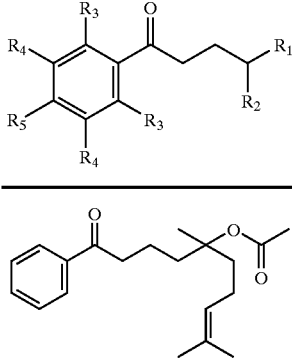 | 9 | Xenon sunlight | 52 60 | 43 44 | | | 47 55 | 46 38 |
| 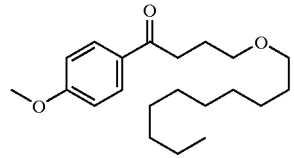 | 10 | Xenon sunlight | 49 37 | 47 37 | | | 34 47 | 44 32 |

All numbers are average values of 3 samples;
[a] n.d. = not determined quantitatively
[b] ca. 0.04 M solution

Example 3

Release of Fragrant Terminal Alkene After Irradiation of Different Phenyl Ketones in a Fabric Softener For this experiment, 0.8 mass-% of precursors 1, 2, 3 and 4 (see Table 1), respectively, were dosed in an unperfumed textile softener containing Esterquats (Stepantex® and Stepanquat®) of the following composition:

| Ingredients | % by weight |
|---|---|
| Stepantex ® VS90 or VHR90* | 16.7 |
| Stepanquat ® F* | 0.4 |
| 1% colorant solution** | 0.3 |
| Water | 82.6 |
| Total | 100.0 |

*Source: Stepan, France
**Sandolan Milling Blue N-LN 180; source: Clariant, Switzerland Cotton towels (28×28 cm) were washed one by one with an unperfumed detergent powder in a Linitest® container. Rinsing with the fabric softener containing either the precursor or a molar equivalent of the corresponding alkene to be released, respectively, was then carried out in a beaker by adding cold water. The towels with the precursors were then compared on a blind test to the one with the corresponding alkene by 13 or 14 panellists after the washing. Each panelist estimated the perceived intensity of the samples on a scale of 1 (no odor) to 10 (very intense odor) and indicated the preferred sample. After being dried at room temperature overnight the towels were exposed to natural indoor daylight (with an average light intensity of 3600 lux) in Pyrex glass containers and the panel evaluation was repeated after 1 day and 6 days, respectively.

Table 2 reports the average intensities perceived by the panellists and between brackets the number of panellists preferring the corresponding sample, obtained in the blind pairwise evaluation of alkenes as compared to their corresponding precursors 1, 2, 3 and 4 respectively.

TABLE 2

| Evaluated sample | No | Wet | Dry (1 day) | Dry (6 days) |
|---|---|---|---|---|
| 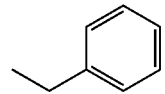 | 1* | 4.0 (6/13) | 2.1 (4/14) | 2.2 (4/13) |
| 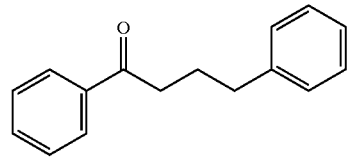 | 1 | 2.3 (5/13) | 2.1 (3/14) | 3.4 (8/13) |
| 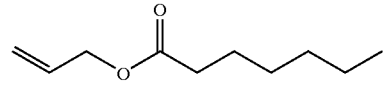 | 2* | 7.9 (12/13) | 2.4 (4/14) | 2.3 (3/13) |
| 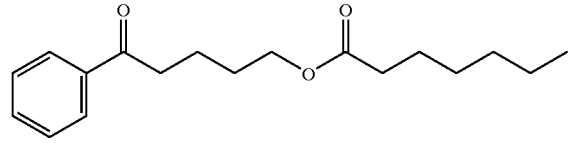 | 2 | 2.8 (1/13) | 2.1 (6/14) | 2.8 (8/13) |
| 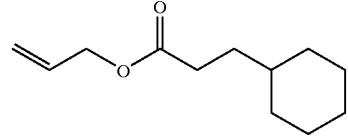 | 3* | 7.6 (12/13) | 2.8 (4/13) | 2.6 (4/14) |
| 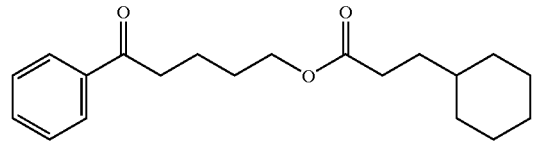 | 3 | 2.1 (1/13) | 2.4 (2/13) | 2.8 (9/14) |

TABLE 2-continued

| Evaluated sample | No | Wet | Dry (1 day) | Dry (6 days) |
|---|---|---|---|---|
| 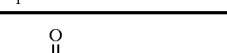 | 4* | 7.3 (9/13) | 3.2 (4/13) | 2.8 (6/14) |
|  | 4 | 2.3 (2/13) | 2.5 (2/13) | 2.6 (8/14) |

Whereas the free perfumery compound was perceived to be very strong on the wet fabric, its intensity decreased rapidly once the towels were dry. In the case of the samples containing the precursor, the odor intensity was judged to remain constant over the time of the experiment, thus nicely illustrated the desired slow release effect. Whereas the panellists generally preferred the unmodified alkenes on the wet fabric, the inverse was observed for the evaluation of the dry towels, where most of the panellists preferred the sample containing the precursor. As example, eight out of 13 panellists preferred the cotton towel with precursor 2 after 6 days of exposure to sunlight and 3 panellists the sample with unmodified alkene 2*. Similar results could be observed with any other type of fabric softener formulations such as those described above.

Example 4

Dynamic Headspace Analysis in all Purpose Cleaners (APC)

In order to follow the perfume release under realistic application conditions, the formation of allyl cyclohexylpropionate and acetophenone from its precursor in an all purpose cleaner (APC) application was investigated by quantitative dynamic headspace analyses. For the experiments, given that the particular nature of the APC base is not relevant within the context of the invention, a standard APC base of the following composition was used:

| Ingredients | % by weight |
|---|---|
| demineralized water | 96.4 |
| Tergitol ® 15-S-12 (ethoxylated secondary alcohol)* | 3.6 |

*origin: Union Carbide, USA

A total of 2.5 g of the APC base containing 0.3 mass-% of the precursor (5-oxo-5-phenylpentyl 3-cyclohexylpropanoate) and 0.3 mass-% of a solubilizer (Triton X 100, Rohm&Haas) were deposed as a thin film on the bottom of a standard glass surface (325×225×50 mm, ≈3.5 l). The surface was exposed to outdoor sunlight for 6 h and continuously flushed with an air stream (58 ml/min). During irradiation, the air flow through the container was decontaminated with a charcoal filter. Every 40 min the volatiles contained in the air stream were adsorbed on 100 mg Tenax® TA cartridges (during 5 min) and the light intensity was measured at the beginning and the end of each sampling with a luxmeter and averaged. Altogether 8 samplings were made. The cartridges were desorbed thermally in a Perkin Elmer TurboMatrix ATD desorber and the volatiles analyzed with a Carlo Erba MFC 500 gas chromatograph equipped with a J&W Scientific DB1 capillary column (15 m, 0.45 mm i.d.) at 70° for 10 min then to 260° (10° C./min) and a He pressure of 50 kPa. The respective concentrations of allyl cyclohexylpropionate and acetophenone released in the headspace were determined by external standard calibrations. The results obtained for a typical experiment are summarized in Table 3 and FIG. 1.

Similar experiments could be carried out on any kind of surface.

TABLE 3

| Time [s] | Amount of Acetophenone Released [ng l$^{-1}$] | Amount of Allyl Cyclohexylpropionate Released [ng l$^{-1}$] | Sunlight Intensity [lux] |
|---|---|---|---|
| 2700 | 3268 | 2922 | 47300 |
| 5400 | 11538 | 4149 | 31895 |
| 8100 | 19110 | 7014 | 66000 |
| 10800 | 24021 | 9881 | 69400 |
| 13500 | 22604 | 9437 | 49100 |
| 16200 | 25385 | 11162 | 52350 |
| 18900 | 25580 | 11788 | 52650 |
| 21600 | 23457 | 11652 | 15575 |

The obtained results clearly show that the desired compounds are released under real daylight conditions from an APC base. Plotting the amount of the fragrances released from the precursor together with the light intensity against time (FIG. 1) nicely illustrates the direct dependency of the perfume release on the intensity of the irradiation. In general, good reproducibility of outdoor sunlight conditions is very difficult to achieve, since the light intensity varies during the day, reaching a maximum value around noon. Furthermore, the appearance of clouds strongly influences the light intensity. The dotted line in FIG. 1 represents ideal sunlight conditions measured at an entirely clear, non clouded day. The first minimum observed in the light intensity curve of the present measurement (after ca 5000 s) is due to short time clouding of the sky during sampling, which does not influence the release of the perfumery compounds. Longer clouding times (as observed between 10000 and 20000 s) however, result in a decrease of fragrance release; as soon as the light intensity re-increases, an increase of both compounds released into the headspace can be observed.

Example 5

Dynamic Headspace Analysis for the Controlled Release on Hair

In order to test the performance of the light induced controlled release of fragrances in typical body care applications, dynamic headspace analysis on hair swatches were carried out. The amount of alkene and acetophenone released from the precursor was compared to the quantity of the corresponding fragrance molecules respectively, using an unperfumed leave-in conditioner base of the following composition:

| Ingredients | % by weight |
|---|---|
| Phytantriol[1] | 0.10 |
| Renex ® 690[2] | 0.50 |
| Propylene glycol | 2.00 |
| D-Panthenol ®[3] | 0.30 |
| Ethoquad O/12[4] | 0.70 |
| Crosilk ® Liquid[5] | 0.10 |
| Mackpro ® NSP[6] | 0.10 |
| Arginine HCl | 0.20 |
| DOW Corning 929 cationic emulsion[7] | 1.00 |
| Kathon ® CG[8] | 0.05 |
| Glydant ®[9] | 0.20 |
| Germall ® II[10] | 0.20 |
| Sodium phosphate | 0.25 |
| Phosphoric acid (42% aq.) | 0.40 |
| Demineralized water | 93.90 |
| Total | 100.00 |

[1] 3,7,11,15-tetramethylhexadecane-1,2,3-triol
[2] nonoxynol-10; origin: ICI Surfactants
[3] origin: Roche
[4] isopropyl alcohol and PEG-2 oleammonium chloride; origin: Akzo Nobel
[5] silk powder; origin: Croda
[6] quaternium-79 hydrolyzed silk; origin: McIntyre
[7] origin: DOW Corning
[8] methylchloroisothiazolinone and methylisothiazolinone; origin: Rohm&Haas
[9] 1,3 bis(hydroxymethyl)-5,5-dimethylimidazolidine-2,4-dione; origin: Lonza
[10] diazolidinyl urea; origin: Sutton This composition is typical of this type of application but the invention is not limited to this particular base and any other base of hair conditioner would be similarly suitable.

total of 0.4 g of the unperfumed leave-on conditioner base containing either 0.33 mass-% of the precursor (5-oxo-5-phenylpentyl 3-cyclohexylpropanoate), 0.20 mass-% of allyl 3-cyclohexylpropanoate or 0.15 mass-% of acetophenone (molar equivalents) and 0.34 mass-% of solubilizer (Renex® 690, origin: ICI Surfactants), respectively, were sprayed in four portions on a lock of hair (≈5 g weight), previously washed with an unperfumed shampoo base. The samples were then irradiated for 3.25 h in a homemade Pyrex® glass tube of approx. 300 ml volume with a Xenon lamp (Heraeus Suntest CPS) at a constant light intensity of ca. 108500 lux and under a constant air flow of 80 ml/min (corresponding to 4 renewals of air/sampling). During irradiation, the glass tube was connected to a charcoal filter for purification. At t=0, 1, 2 and 3 h the constituents of the headspace were adsorbed for 15 min onto 100 mg Tenax® TA cartridges. The cartridges were desorbed thermally with a Perkin Elmer ATD 400 desorber and the volatiles analyzed with a Perkin Elmer Autosystem XL gas chromatograph. The analyses were effected using a Supelco SPB-1 capillary column (30 m, 0.53 mm i.d., film 1.5 micron) from 60° to 250° (10°/min) with He as carrier gas at a linear velocity of 25 cm/sec. Results are shown in Table 4 and FIG. 2

TABLE 4

Comparison of the dynamic headspace of free acetophenone and allyl cyclohexylpropanoate and their respective precursors in a leave-on hair conditioner irradiated with a Xenon lamp

| Time [h] | Amount of free Acetophenone [ng $l^{-1}$] | Amount of free Allyl 3-cyclo-hexyl-propanoate [ng $l^{-1}$] | Amount of Acetophenone Released [ng $l^{-1}$] | Amount of Allyl 3-cyclohexyl-propanoate Released [ng $l^{-1}$] |
|---|---|---|---|---|
| 0 | 27890 | 15290 | 1350 | 530 |
| 1 | 17220 | 3600 | 1570 | 980 |
| 2 | 5770 | 800 | 1510 | 950 |
| 3 | 3210 | 340 | 1400 | 790 |

Figure 2:
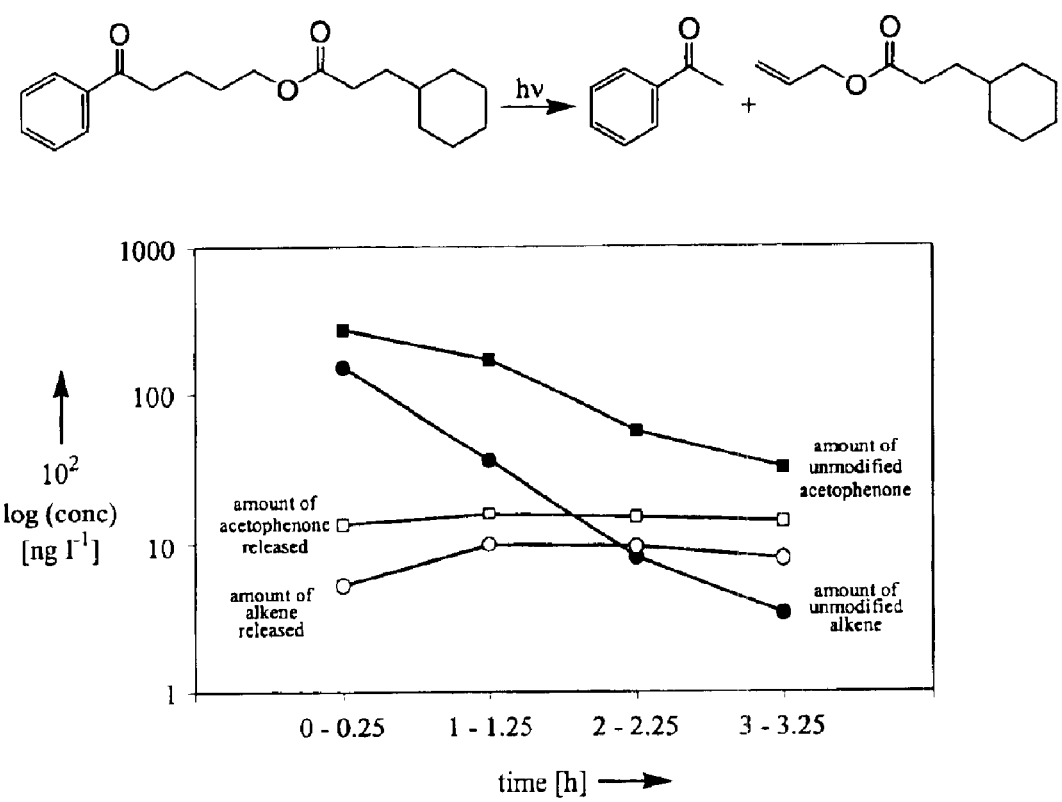
FIG. 2 is a graph that illustrates light induced controlled release of alkene and acetophenone from its precursor as measured from hair swatches by quantitative dynamic headspace analyses.

FIG. 2 and Table 4 illustrate that the concentration of free allyl 3-cyclohexylpropanoate and acetophenone decrease rapidly with time, whereas the amount of the corresponding compounds released from the precursors remain almost constant during the experiment (at constant light intensity). After ca. two hours of irradiation, the concentration curve of allyl 3-cyclohexylpropanoate released from the precursor crosses the concentration curve of the unprotected alkene, thus illustrating that the desired long lasting effect of the precursor system becomes efficient after a relatively short irradiation time.

What is claimed is:

1. Perfuming, masking, antimicrobial, insect repelling or insect attracting composition or product comprising, together with one or more perfuming ingredients, masking agents, antimicrobial agents, insect repelling or attracting ingredients, solvents or adjuvants of current use, at least one compound of formula

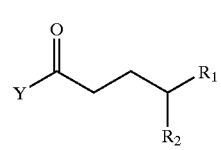

(I)

wherein

Y represents a pyridyl group, or a phenyl group of formula

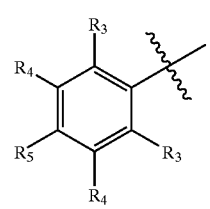

(Ia)

wherein $R_3$ represents a hydrogen atom, a $CF_3$ group or a linear or branched alkoxy group from $C_1$ to $C_{12}$, $R_4$ represents a hydrogen atom, a linear or branched alkyl group from $C_1$ to $C_4$, or a $CF_3$ group, $R_5$ represents a hydrogen atom, a linear or branched alkyl group from $C_1$ to $C_4$, a $CF_3$ group or a linear or branched alkoxy group from $C_1$ to $C_{12}$; and $R_1$ and $R_2$ are the substituents of an active perfuming, masking, antimicrobial, insect repelling or attracting terminal alkene of formula (i)

(i)

wherein $R_1$ represents a linear or branched alkyl or alkylene group from $C_1$ to $C_{35}$, an unsubstituted or substituted mono- or poly-cycloalkyl group having 3 to 8 carbon atoms, or an unsubstituted or substituted phenyl group, said alkyl, alkylene, mono- or poly-cycloalkyl and phenyl groups possibly comprising one or several hetero-atoms selected from the group consisting of oxygen, nitrogen, phosphorous and sulfur; and $R_2$ represents a hydrogen atom, a linear or branched alkyl or alkylene group from $C_1$ to $C_{35}$, an unsubstituted or substituted mono- or poly-cycloalkyl group from $C_3$ to $C_8$, or an unsubstituted or substituted phenyl group, said alkyl, alkylene, mono- or poly-cycloalkyl and phenyl groups possibly comprising one or several hetero-atoms selected from the group consisting of oxygen, nitrogen, phosphorous and sulfur.

2. Composition or product according to claim 1 in the form of a perfuming composition or product comprising, together with one or more perfuming ingredients, solvents or adjuvants of current use in perfumery, at least one compound of formula (I) as defined in claim 1, wherein $R_1$ and $R_2$ are the substituents of an active perfuming terminal alkene of formula (i) as defined in claim 1.

3. Composition or product according to claim 2, wherein $R_1$ represents a linear or branched alkyl or alkylene group from $C_1$ to $C_{20}$, an unsubstituted or substituted mono- or poly-cycloalkyl group from $C_3$ to $C_8$, or an unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulfur; and $R_2$ represents a hydrogen atom, a linear or branched alkyl or alkylene group from $C_1$ to $C_{20}$, an unsubstituted or substituted mono- or poly-cycloalkyl group from $C_3$ to $C_8$, or an unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulfur.

4. Composition or product according to claim 1, comprising at least one compound of formula (I) as defined in claim 1, wherein Y represents a phenyl group of formula (Ia) as defined in claim 1.

5. Composition or product according to claim 4, comprising at least one compound of formula

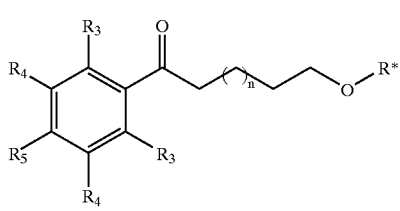
(II)

wherein $R_3$, $R_4$, and $R_5$ have the same meaning as in formula (I), n is an integer varying from 0 to 10, and R* represents a hydrogen atom, a linear or branched alkyl or alkylene group from $C_1$ to $C_{20}$, an unsubstituted or substituted mono- or poly-cycloalkyl group from $C_3$ to $C_8$, or unsubstituted or substituted phenyl group, wherein said alkyl, alkylene, mono- or poly-cycloalkyl and phenyl groups may comprise one or several hetero-atoms selected from the group consisting of oxygen, nitrogen, phosphorous and sulfur.

6. A method for generating a specific activity of a perfuming, masking, antimicrobial, insect repelling or attracting nature coming from a surface selected from the group consisting of skin or hair, floor, window, tile, furniture, fabric or cloth, or a plant, which comprises treating the surface with a compound of formula (I) as defined in claim 1, or with a composition or product according to claim 1, and exposing the surface to light to generate the activity by releasing the terminal alkene.

7. A method for generating a specific activity of the perfuming, masking, antimicrobial, insect repelling or attracting nature on a surface selected from the group consisting of skin or hair, floor, window, tile, furniture, fabric or cloth, or a plant, which comprises treating said surface with a compound of formula (II) such as defined in claim 5, or with a composition or product according to claim 5, and exposing said surface to light to release the terminal alkene.

8. A method according to claim 6, wherein the specific activity is the perfuming of the surface.

9. A method according to claim 7, wherein the specific activity is the perfuming of the surface.

10. Composition or product according claim 1, in the form of an air-freshener, all purpose cleaner, furniture polish, detergent, fabric conditioner, fabric softener, soap, bath or shower gel, cosmetic preparation, body deodorant, perfume or cologne.

11. Precursor of an active perfuming, masking, antimicrobial, insect repelling or attracting molecule, said precursor being represented by the following formula:

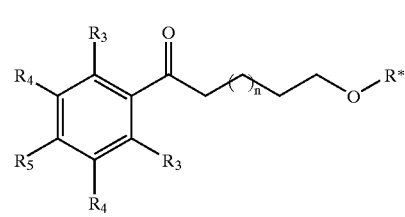
(II)

wherein $R_3$, $R_4$, and $R_5$ have the same meaning as in formula (I) as defined in claim 1, n is 1 or greater, and R* represents a linear or branched alkylene group from $C_5$ to $C_{20}$ or a branched alkyl group from $C_3$ to $C_{20}$, an unsubstituted or substituted mono- or poly-cycloalkyl group from $C_3$ to $C_8$, or substituted phenyl group, wherein said branched alkyl, linear or branched alkylene, mono- or poly-cycloalkyl and substituted phenyl groups may comprise one or several hetero-atoms selected from the group consisting of oxygen, nitrogen, phosphorous and sulfur, provided that when R* represents a mono-cycloalkyl group that is optionally substituted by a hetero atom, the hetero atom is not a single oxygen atom.

12. A surface selected from the group consisting of skin or hair, floor, window, tile, furniture, fabric or cloth and plant, that has been treated with a compound of formula (I) as defined in claim 1, or with a composition or product according to claim 1, and then is exposed to light to release the terminal alkene.

13. Precursor of an active perfuming, masking, antimicrobial, insect repelling or attracting molecule, the precursor being 5-oxo-5-phenylpentyl heptanoate, 5-oxo-5-phenylpentyl 3-cyclohexylpropionate, 5-oxo-5-phenylpentyl phenoxyacetate, 1,5-dimethyl-1-(4-oxo-4- phenylbutyl)-4-hexenyl acetate, 4-(decyloxy)-1-(4-methoxyphenyl)-1-butanone, 1-(4-methoxyphenyl)-4-(2-phenylethoxy)-1-butanone, 4-(decyloxy)-1-(4-methylphenyl)-1-butanone, 1-(4-methylphenyl)-4-(2-phenylethoxy)-1-butanone, or 1-(4-tert-butylphenyl)-4-(2-phenylethoxy)-1-butanone.

14. Precursor of an active perfuming, masking, antimicrobial, insect repelling or attracting molecule, said precursor being represented by the following formula:

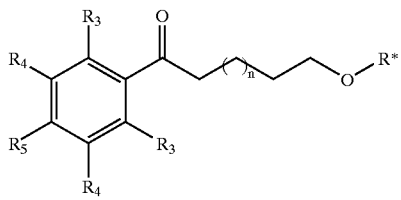

(II)

wherein $R_3$, $R_4$, and $R_5$ have the same meaning as in formula (I) as defined in claim 1, n is 0, and R* represents a branched alkylene group from $C_5$ to $C_{20}$, an unsubstituted or substituted or mono- or poly-cycloalkyl group from $C_3$ to $C_8$, or a substituted phenyl group, wherein said branched alkylene, mono- or poly-cycloalkyl or substituted phenyl groups may comprise one or several hetero-atoms selected from the group consisting of oxygen, nitrogen, phosphorous and sulphur, provided that when R* represents a mono-cycloalkyl group that is optionally substituted by a hetero atom, the hetero atom is not a single oxygen atom.

* * * * *